United States Patent [19]
Premuzic et al.

[11] Patent Number: 5,366,891
[45] Date of Patent: Nov. 22, 1994

[54] BIOCHEMICAL SOLUBILIZATION OF TOXIC SALTS FROM RESIDUAL GEOTHERMAL BRINES AND WASTE WATERS

[75] Inventors: Eugene T. Premuzic, East Moriches; Mow S. Lin, Rocky Point, both of N.Y.

[73] Assignee: Associated Universities, Inc., Washington, D.C.

[21] Appl. No.: 115,760

[22] Filed: Sep. 3, 1993

Related U.S. Application Data

[63] Continuation-in-part of Ser. No. 853,199, Mar. 18, 1992, abandoned.

[51] Int. Cl.$^5$ .......................... B09B 3/00; C12N 1/12; C02F 3/00
[52] U.S. Cl. .................. 435/262; 435/262.5; 435/252.1; 423/1; 423/27; 75/392
[58] Field of Search .................. 435/262, 262.5, 252.1; 423/1, 27, 41, DIG. 17, 106; 75/392

[56] References Cited

U.S. PATENT DOCUMENTS

| | | | |
|---|---|---|---|
| 2,829,964 | 4/1958 | Zimmerley et al. | 75/104 |
| 3,433,629 | 3/1969 | Imal et al. | 75/101 |
| 4,033,763 | 7/1977 | Markels, Jr. | 75/97 |
| 4,530,763 | 7/1985 | Clyde et al. | 210/610 |
| 4,664,804 | 5/1987 | Morper et al. | 210/605 |
| 4,725,357 | 2/1988 | Downing et al. | 210/611 |
| 4,729,788 | 3/1988 | Hutchins et al. | 75/2 |
| 4,732,608 | 3/1988 | Emmett, Jr. et al. | 75/101 |
| 4,740,243 | 4/1988 | Krebs-Yuill et al. | 75/101 |
| 4,752,332 | 6/1988 | Wu et al. | 75/101 |
| 4,758,345 | 7/1988 | Francis et al. | 210/611 |
| 4,789,478 | 12/1988 | Revis et al. | 210/611 |

OTHER PUBLICATIONS

Premuzik et al. "Advanced Biochemical Processes for Geothermal Brines", Annual Report FY1989 BNL-43693 pp. 1-30.
Lin et al., "Detoxofication of Residual Brine Sludges Derived from Geothermal Power Plants", in Heavy Metals in the Environment, vol. 1, Eds: Lindberg and Hutchinson, International Conference, New Orleans, pp. 448-450, Sep. 1987.
Premuzic, et al., "Some Aspects of Geothermal Waste Treatment Biotechnology", in Geothermal Resources Council, Transactions, vol. 12, Oct. 1988.
Premuzic, et al., "Regional Variation in the Metal Composition of Residual Brine Sludges Derived from Geothermal Power Plants", in Geotherm. Sci. & Tech., 1989, vol. 2(2), pp. 125-137.
Premuzic, et al., "The Role of Biotechnology in the Treatment of Geothermal Residual Sludges", Presented at the Heavy Metals in the Environmental International Conference, Geneva, Switzerland, Sep. 12-15, (1989).
Premuzic, et al., "Developments in Geothermal Waste Treatment Biotechnology", proceedings in the National Energy Strategy-The Role of Geothermal Technology Development, Apr. 18-20, 1990, San Francisco, Calif.
Premuzic, et al., "Progress in Geothermal Waste Treatment Biotechnology", Transactions, vol. 15, Oct. 1991.

*Primary Examiner*—Michael G. Wityshyn
*Assistant Examiner*—Timothy J. Reardon
*Attorney, Agent, or Firm*—Margaret C. Bogosian

[57] ABSTRACT

A method of solubilizing metal salts such as metal sulfides in a geothermal sludge using mutant Thiobacilli selected for their ability to metabolize metal salts at high temperature is disclosed, The method includes the introduction of mutated *Thiobacillus ferrooxidans* and *Thiobacillus thiooxidans* to a geothermal sludge or brine. The microorganisms catalyze the solubilization of metal salts, For instance, in the case of metal sulfides, the microorganisms catalyze the solubilization to form soluble metal sulfates.

13 Claims, 29 Drawing Sheets

BIOCHEMICAL SOLUBILIZATION OF TOXIC SALTS FROM RESIDUAL GEOTHERMAL BRINES AND WASTE WATERS

This invention was made with Government support under contract number DE-AC02-76CH00016, between the U.S. Department of Energy and Associated Universities, Inc. The Government has certain rights in the invention.

This application is a continuation-in-part of U.S. patent application Ser. No. 07/853,199 filed Mar. 18, 1992, now abandoned.

BACKGROUND OF THE INVENTION

The production of electricity through the conversion of energy from underground geothermal reservoirs is a growing industry. Unfortunately, large scale production of electricity from geothermal sources produces considerable amounts of waste in the form of residual brine sludges. These sludges contain varying concentrations of toxic metals which require expensive disposal at hazardous waste disposal sites.

Hydrothermal systems utilize subsurface reservoirs of either steam (vapor-dominated) or hot water (liquid-dominated). Water in these systems is usually derived from surface water that percolates downward through sediments or fissures to a heat source such as hot dry rock or molten magma. The heated water then rises toward the surface in the form of geysers or hot springs. If the pressure on the water within the reservoir is insufficient to prevent boiling, a vapor phase consisting of dry or super-heated steam will form. Such a system is readily exploitable for generating electricity.

When the pressure exceeds the vapor pressure of the brine in the reservoir there is little vapor phase, resulting in a liquid-dominated hydrothermal system. Liquid-dominated hydrothermal systems are more difficult to utilize directly since they contain dissolved mineral salts which pose serious scaling and corrosion problems in production equipment and injection wells.

The brine from a liquid-dominated system is usually flashed (i.e., pressure is released resulting in an instantaneous expansion to a vapor phase) to a vapor which drives a turbine. The residual liquid brine from the flash may contain precipitated solids that render the residual liquid brine inappropriate for reinjection into a reservoir (due to the potential for injection well-clogging). The precipitated waste solids may be removed by a clarifier and the brine may be filtered. After filtering, the brine can be reinjected.

Geothermal power plants also generate waste during well drilling and plant operations. Well drilling waste consists of drilling muds, brines, and residues and operational waste consists of cooling tower and separator blown down sludges. These slurries and brines also pose serious problems for reinjection. Additionally, many of these precipitated solids are toxic.

The chemical composition of geothermal brine fluids varies greatly, is source specific, and can vary over time. Geothermal brine fluids may contain a number of different dissolved metals such as chromium, vanadium, titanium, antimony, nickel, bismuth, tin, silver, cadmium, beryllium, selenium and others. These solids precipitate out during the processing of the superheated fluids, are highly concentrated and enriched in a variety of salts.

Safe waste disposal is of increasing concern worldwide. In California for example, all solid waste produced in the Imperial Valley must be analyzed for regulated substances using the California Department of Health Services (DOHS) standard analytical techniques. "Identification and Listing of Hazardous Waste Under RCRA (Resource Conservation and Recovery Act)", Subtitle C, Section 3001, EP Toxicity Characteristics, USEPA. (May 1980). A solid waste is deemed hazardous if it contains a regulated substance (e.g., Zn, Cr, Pb, As, Cu) at a level exceeding the total threshold limit concentration (TTLC). Waste is also considered hazardous if the leachable level of any regulated substance is above the DOHS soluble threshold limit concentration (STLC). The California Department of Health Services (DOHS) Soluble and Total Threshold Limit Concentrations (STLC and TTLC) calculated by standard analytic techniques (EPA, 1980) are shown in Table 1.

TABLE 1

The California DOHS Soluble and Total Threshold Limit Concentration Values of Inorganic Toxic Substances in Hazardous Waste

| Inorganic Substances | STLC (mg/l) | TTLC (mg/kg) |
|---|---|---|
| Antimony and/or antimony compounds | 15 | 500 |
| Arsenic and/or arsenic compounds | 5.0 | 500 |
| Barium and/or barium compounds (excluding barite) | 100 | 10,000* |
| Beryllium and/or beryllium compounds | 0.75 | 75 |
| Cadmium and/or cadmium compounds | 1.0 | 100 |
| Chromium (VI) compounds | 5 | 500 |
| Chromium and/or chromium (III) compounds | 560 | 2,500 |
| Cobalt and/or cobalt compounds | 80 | 8,000 |
| Copper and/or copper compounds | 25 | 2,500 |
| Flouride salts | 180 | 18,000 |
| Lead and/or lead compounds | 5.0 | 1,000 |
| Mercury and/or mercury compounds | .2 | 20 |
| Molybdenum and/or molybdenum compounds | 350 | 3,500 |
| Nickel and/or nickel compounds | 20 | 2,000 |
| Selenium and/or selenium compounds | 1.0 | 100 |
| Silver and/or silver compounds | 5 | 500 |
| Thallium and/or thallium compounds | 7.0 | 700 |
| Vanadium and/or vanadium compounds | 24 | 2,400 |
| Zinc and/or zinc compounds | 250 | 5,000 |

* excluding barium sulfate

Note: STLC and TTLC values are based on the concentrations of the elements, not the compounds. TTLC values are calculated on a wet-weight basis. The limits of elemental metals apply only if the substances are in a friable, powdered, or finely divided state.

Due to the high cost of hazardous solid-waste disposal and the long-term liability, the continued use of hypersaline geothermal brines in the production of electricity hinges upon the reduction or elimination of toxic solid-waste generation.

Microbial leaching (bioleaching) of low-grade ores using bacteria of the genus Thiobacillus (T.) has been utilized by the mining industry for the recovery of copper and uranium. Microbial leaching involves the dissolution of soluble materials catalyzed by microorganisms. Thiobacilli oxidize certain metallic sulfides into water-soluble sulfates by acting as catalysts in the production of sulfuric acid from elemental sulfur (LeRoux, N. W., *New Scientist*, pp. 12–14, (September 1969)).

Most Thiobacilli are mesophilic, i.e., they thrive at moderate temperatures. Both *T. ferrooxidans* and *T. thiooxidans* are chemolithotrophic or "rock-eating", i.e., they obtain their energy from the oxidation of inorganic compounds found in rock. Both species of bacteria obtain their carbon requirements from carbon dioxide in the air, i.e., they are autotrophic (Brierly, C. L., *Science* 78:44-53 (1978)).

*Thiobacilli ferrooxidans* and *Thiobacilli thiooxidans* bioleach metals into solution via different mechanisms. *T. ferrooxidans* solubilizes metals through a series of oxidation-reduction reactions to form soluble metal sulfates (Kelly, O. P. and C. A. Jones, *Metallurgical Applications of Bacterial Leaching and Related Microbiological Phenomena*, Academic Press, New York, pp. 19-43 (1978)).

*T. ferrooxidans* are gram-negative nonsporing rod-like organisms measuring 0.5-0.7 $\mu$m, which move about using a single polar flagella. Their energy requirements are met by the oxidation of inorganic sulfur, sulfide compounds, and iron compounds (Silver, M., *Metallurgical Applications of Bacterial leaching and Related Microbiological Phenomena*, Academic Press, New York, pp. 19-43 (1978)). *T. ferrooxidans* solubilizes certain metal ions through the following oxidation-reduction reactions (Bosecker, K and Kursten, M., *Process Biochemistry*, pp. 2-4 (October 1978)).

$$2FeS_2 + 7O_2 + 2H_2O \rightarrow 2FeSO_4 \quad (1)$$

$$4FeSO_4 + O_2 + 2H_2SO_4 \rightarrow 2Fe_2(SO_4)_3 + 2H_2O \quad (2)$$

$$MS + Fe_2(SO_4)_3 \rightarrow MSO_4 + 2FeSO_4 + S° \quad (3)$$

$$2S° + 3O_2 + 2H_2O \rightarrow 2H_2SO_4 \quad (4)$$

where M is the metal of interest. Reactions (1), (2), and (4) are catalyzed by *T. ferrooxidans*. Reaction (3) proceeds in the absence of bacteria. Ferric ions produced from the oxidation of ferrous ions in reaction (2) are reduced in reaction (3). The insoluble metal sulfides are oxidized in reaction (3) to produce metal sulfates and elemental sulfur. The elemental sulfur produced in reaction (3) is then oxidized in reaction (4) to form sulfuric acid. In the absence of iron, the acid produced can oxidize metal sulfides. Leaching is accomplished because the sulfates produced are soluble.

*T. thiooxidans* are gram negative, rod shaped bacteria 1.0-2.0 $\mu$m long and 0.5 $\mu$m across. Like *T. ferrooxidans*, they also move about by means of a single, polar flagellum. *T. thiooxidans* also oxidize elemental sulfur and thiosulfate, but are incapable of oxidizing iron (Cripps, R. E., *Extern*, 9(40):200-216 (1980)). These bacteria catalyze the formation of sulfuric acid via reaction (4). The sulfuric acid thus generated solubilizes metal sulfides by the following reaction:

$$2MS + 2H_2SO_4 + O_2 \rightarrow 2MSO_4 + 2H_2O + 2S° \quad (5)$$

Reactions (4) and (5) constitute the Thiobacillus catalyzed acid leaching cycle.

It is known that mixed cultures of *T. ferrooxidans* and *T. thiooxidans* are more effective than either organism alone in the leaching of certain ores. This is due to the complementary nature of reactions (2) to (4). The elemental sulfur generated in reaction (3) is oxidized by both *T. thiooxidans* and *T. ferrooxidans* in reaction (4) to produce sulfuric acid. However, none of the above-references teach or suggest the treatment of geothermal waste.

It has been previously shown by the subject inventors that acidophilic microorganisms can be used as the "active agents" in the detoxification of geothermal brine residues. A preliminary design for a process has been suggested and a technical and feasibility study of this process has been earlier described by the subject inventors (Premuzic, et al., *Geothermal Resources Council, TRANSACTIONS*, Vol. 12 (October 1988)). The efficiency of metal sulfide solubilization by several strains of *Thiobacillus thiooxidans* and *Thiobacillus ferrooxidans* was also studied.

Acidophilic bacteria have been used to leach sulfide minerals such as zinc and copper. For example, U.S. Pat. No. 2,829,964 to Zimmerley, et al. describes a cyclic process involving the use of a ferric sulfate sulfuric acid solution carrying cultures of iron oxidizing autotrophic bacteria. The bacteria involved appear akin to *Thiobacillus ferrooxidans*. The bacteria were bred in successively greater concentrations of dissolved metals, resulting in strains of bacteria which tolerate relatively high metal concentrations. The bacterial leaching process may be enhanced by the addition of certain nutrients to the leaching solution. Zimmerley, et al. do not however teach or suggest the treatment of waste and do not use mixed strains of Thiobacillus.

U.S. Pat. No. 3,433,629 to Imai, et al. describes the use of *Thiobacillus thiooxidans* for dissolving and recovering manganese in the form of water soluble salts from manganese ores. The use of mixed cultures of Thiobacillus is not taught or suggested and the patent does not address geothermal waste treatment.

U.S. Pat. No. 4,033,763 to Markels describes the recovery of metals from waste waters by bacterial action. There is very little discussion as to what type of bacteria is used and *Thiobacillus ferrooxidans* and *Thiobacillus thiooxidans* are not mentioned. Markels uses "sewage-type" bacteria to imbibe metals in a sludge (i.e., the metals are not dissolved).

U.S. Pat. No. 4,530,763 to Clyde discloses the use of *Thiobacillus ferrooxidans* to remove palladium from waste fluid. *Thiobacillus ferrooxidans* is attached to a porous fiber webbing. Palladium then attaches (it is not dissolved) to the *Thiobacillus ferrooxidans* when the webbing is contacted with waste fluid. After a sufficient period of time, the webbing is removed from the fluid and palladium is separated from the webbing.

U.S. Pat. No. 4,664,804 to Morper, et al. describes a process for the removal of heavy metals from waste water. In this process, anaerobic sludge is added to the waste water. Contrary to solubilization, heavy metals are absorbed (not dissolved) by the anaerobic sludge and are thereafter separated from the sludge.

U.S. Pat. No. 4,725,357 to Downing, et al. describes a process for the removal of dissolved selenium from water by treatment in a reactor containing a microbial Bacillus biomass. Downing, et al. do not address metal sulfide dissolution by microbial action.

U.S. Pat. No. 4,732,608 to Emmett, Jr., et al. describes a method and apparatus for use in a bioleaching process for metal bearing solids (such as a mineral ore). The method encompasses the placement into a tank of a grounded metal bearing solid, water, oxygen, carbon dioxide, nutrients and a species of microorganism capable of oxidizing some portion of the metal bearing solid and obtaining energy from that oxidation. Emmett, Jr., et al. disclose the use of *Thiobacillus ferrooxidans* and *Thiobacillus thiooxidans* in leaching treatments for the solubilization of copper from low grade ores. The Emmett, Jr., et al. apparatus includes a plurality of bioreactor vessels with a means for introducing air bubbles into the slurry and a plurality of radial arms which rotate and agitate the slurry. The process and apparatus are specifically directed for use in processing precious metal-bearing pyrites. The process and apparatus may be used for leaching gold, silver and platinum from sulfide containing ore solids, but are not used in the treatment of geothermal waste.

U.S. Pat. Nos. 4,740,243 to Krebs-Yuill, et al. and 4,752,243 to Wu, et al. describe processes for recovering metal from a metal sulfide containing ore with *Thiobacillus ferrooxidans*. This involves contacting an ore with an aqueous acidic composition and at least one reducible manganese-containing material in the presence of *Thiobacillus ferrooxidans*. By normal acclimation techniques, the manganese tolerance of the bacteria is increased to greater than about 4 weight per cent. Neither of these disclosures relate to the dissolution of metals in a geothermal sludge, but rather describe leaching metals (such as gold and silver) from a metal sulfide containing ore.

No prior art describes a process for the dissolution of metal sulfides in a geothermal sludge involving the use of *Thiobacillus ferrooxidans*. Nor does any describe an apparatus for use in the bioleaching of metals from a geothermal sludge.

An object of the present invention is to remove precipitated solids from a geothermal brine or sludge through bioleaching. Since the subject processes are readily (and economically) suitable for commercial application, the subject invention presents a solution to a long felt need in the art.

A second object of the present invention is to provide a biological treatment at high temperatures, 50°–60° C. or even higher, for geothermal brine or sludge which renders the geothermal sludge non-toxic and lowers the cost of waste disposal.

By employing the methods and bacteria of the subject invention, it is possible to biologically reduce the toxic metal content by reducing the concentration of metal sulfides and other metal salts in a geothermal sludge or brine. In addition, this treatment reduces the toxicity of the sludge or brine and minimizes the cost of toxic waste removal by decreasing the amount and volume of toxic waste produced.

Further, by reducing the amount of solid metal salts, the present invention diminishes the scaling and clogging of pipes or other conduits used to transport brine or sludge.

The subject low-cost processes for the removal of toxic metals from and volume reduction of geothermal residues include:

1. efficient removal of metals by means of biochemical processes;
2. the flexibility to be operated at different temperatures and sludge concentrations;
3. identification of key process variables; and
4. cost-efficiency in the detoxification process.

SUMMARY OF THE INVENTION

The subject invention comprises contacting metal salts, such as a metal sulfide, with *Thiobacillus ferrooxidans* and/or *Thiobacillus thiooxidans* for a time sufficient to solubilize the metal sulfide by forming a soluble metal sulfate. The Thiobacillus used in the subject invention are preferably selected so as to effectively metabolize metal salts at high temperatures. Preferred *Thiobacillus ferrooxidans* microorganisms are selected from the group of ATCC #53982, ATCC #53983, ATCC #53984, ATCC #53985, ATCC #53986, ATCC #53987 and preferred *Thiobacillus thiooxidans* microorganisms are selected from the group of ATCC #55019, ATCC #55020, ATCC #53990 and ATCC #55009. Most preferably, the *Thiobacillus ferrooxidans* is ATCC #53987 and the *Thiobacillus thiooxidans* is ATCC #55020.

Microorganisms typically are grown separately and then added to the sludge when they are at maximum growth. The biochemical process is allowed to continue for 5½ to 25 weeks, depending upon initial concentration and then processed following the approach shown in FIG. 2.

DEPOSIT

Figure 1:
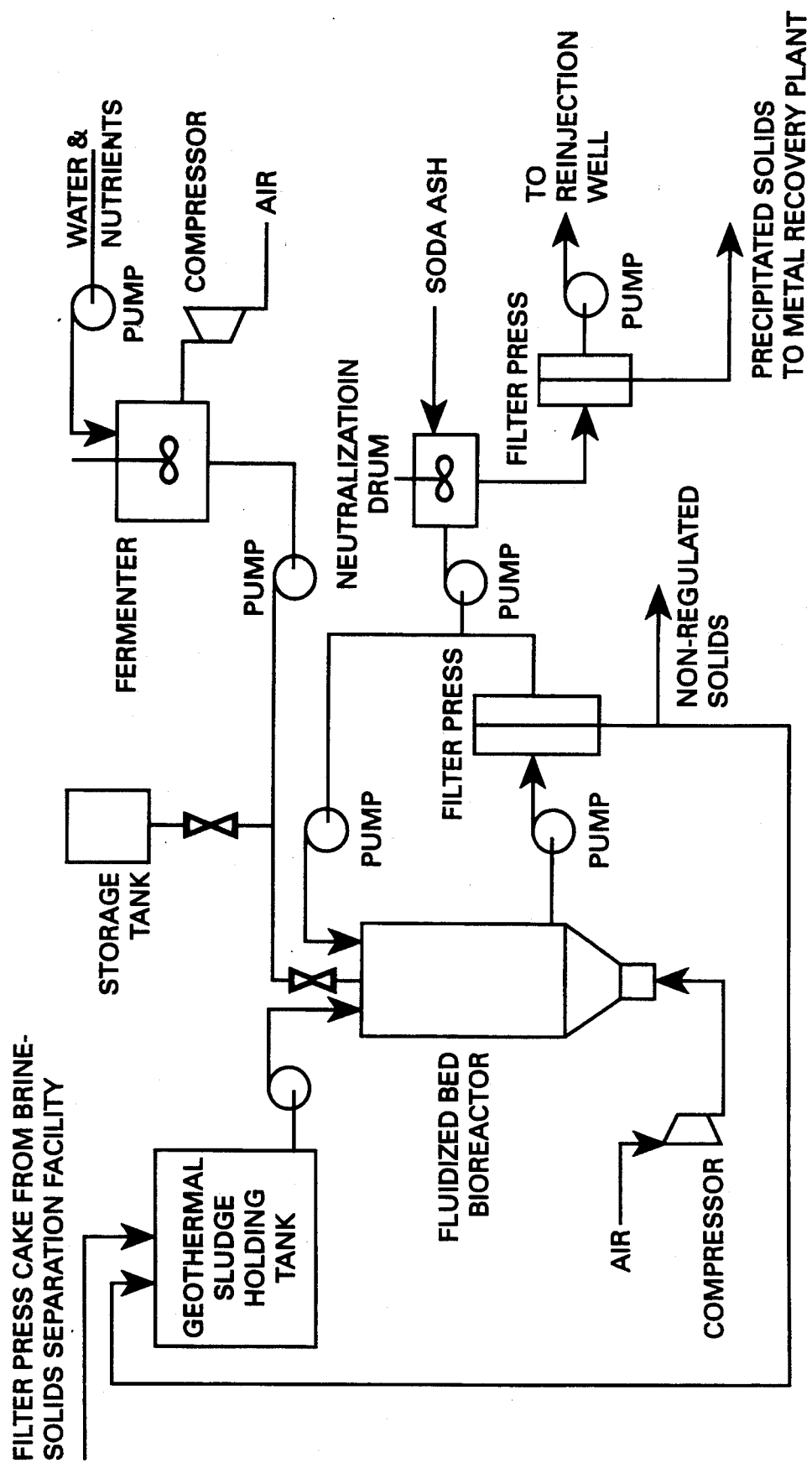
FIG. 1 depicts a flow diagram for a waste treatment plant which can use either a fluidized bed bioreactor or an agitated tank.

A number of microorganisms, grown and adapted for purposes of the present invention and illustrative of the modified microorganisms useful in the biological solubilization process of the present invention have been deposited in the American Type Culture Collection, Rockville, Md. 20852, prior to the filing date of this application and in accordance with the permanency and accessibility requirements of the U.S. Patent and Trademark Office. The following is a list of such deposited microorganisms:

| Scientific Description | Applicant's Reference | ATCC Designation | Date of Deposit |
|---|---|---|---|
| Thiobacillus ferrooxidans | BNL-2-44 | 53982 | 12/19/89 |
| Thiobacillus ferrooxidans | BNL-2-45 | 53983 | 12/19/89 |
| Thiobacillus ferrooxidans | BNL-2-46 | 53984 | 12/19/89 |
| Thiobacillus ferrooxidans | BNL-2-47 | 53985 | 12/19/89 |
| Thiobacillus ferrooxidans | BNL-2-48 | 53986 | 12/19/89 |
| Thiobacillus ferrooxidans | BNL-2-49 | 53987 | 12/19/89 |
| Thiobacillus thiooxidans | BNL-3-25 | 53990 | 12/19/89 |
| Thiobacillus thiooxidans | BNL-3-26 | 55009 | 1/25/90 |
| Thiobacillus thiooxidans | BNL-3-23 | 55019 | 3/22/90 |
| Thiobacillus thiooxidans | BNL-3-24 | 55020 | 3/22/90 |
| Pseudomonas sp. | BNL-4-24 | 55024 | 3/22/90 |
| Sulfalobus solfataricus | BNL-TH-29 | 55022 | 3/22/90 |
| Sulfalobus solfataricus | BNL-TH-31 | 55023 | 3/22/90 |

DETAILED DESCRIPTION OF THE INVENTION

The subject invention will now be described in terms of its preferred embodiments. These embodiments are set forth to aid in the understanding of the subject invention, but are not to be construed as limiting.

The subject invention is predicated on the use of biochemical methods for dissolution of toxic elements found in geothermal residues. Based on the subject disclosure, an environmentally satisfactory and economically practical commercial detoxification plant may be created. Utilizing the subject invention, a solution containing toxic metals can be reinjected or used for concentrating and recovering metals.

Mixtures of selected strains of thermophilic and acidophilic bacteria were pre-grown and then introduced into a bioreactor, where they were found to be more efficient then each strain alone. Better than 80% removal of toxic metals at 50°-60° C. was achieved by using mixed cultures. By optimizing conditions for the use of mixed cultures and selecting for high temperature mutant strains of Thiobacillius, decreased bioreactor residence times and an overall cost reduction is realized.

To obtain a better understanding of the influence of type and size of bioreactors on the cost and efficiency of a biochemical waste treatment plant, an economic analysis of processes for the detoxification of geothermal sludges was conducted. Two processes were considered, one based on a fluidized bed and the other on an agitated tank bioreactor.

The proposed biochemical waste treatment process was based on 80,000 lb/day of dry geothermal waste contained in a 65% filter press cake from a 50 MW double flash plant (the following economic analysis was previously published in Premuzic, E. T., et al., *Geothermal Resources Council, TRANSACTIONS*, Vol. 15 (October, 1991), the contents of which are hereby incorporated by reference).

A process flow diagram for the proposed biological waste treatment facility using a fluidized bed bioreactor (or air lift bioreactor) is depicted in FIG. 1. The filter press cake (65% of solid) from a brine-solids separation plant is sent to the fluidized bed bioreactor by a conveyor belt at an average rate of 123,000 lb/day.

In this process, bacteria are continuously added to keep a high cell concentration and a low culture medium pH in the reactor. The fermentor and bacterial cultures storage tank connected to the biological waste treatment plant are used to grow and store cultures until they are needed.

Interaction between microbial biomass and geothermal sludge takes place in the bioreactor where the solid and liquid are well mixed during the residence time. The bioreactor outflow (stream 4) containing solids, is sent to filter press where it is concentrated to a 65% solid cake, which is a nonhazardous solid waste product. In the event that the solid product is still hazardous, the filter press cake is recycled to geothermal sludge holding tank (stream 5) and reprocessed.

If necessary, liquid which passes through the filter press can be recycled back to the bioreactor (stream 3), or is sent to a neutralization drum (stream 6) where pH 4 is maintained. The liquid is then pumped through a filter in order to collect any washed out bacteria and precipitated solids from the neutralization process. The filtrate from filter press 2 is then pumped down a reinjection well (stream 9). Any precipitated solids which were collected by filter press 2 may be sent to the metal recovery plant as another alternative process to be considered in the future.

The streams of biochemical waste treatment plant for the fluidized bed and the agitated tank bioreactor are summarized in Table 2 for various solid loadings. For these experiments, calculations based on the production of geothermal sludge at a rate of 5130 lb/hr in a 50-MW power plant. The volume of a reactor depends on the process design, the residence time and solid loading. The generalized expression relating reactor volume to a certain amount of geothermal sludge production for a geothermal electric power plant is given by equations (1) and (2).

$$F = XY/W - X(1 - 0.01Y) \tag{1}$$

$$V = (SF)(0.12\ FR + 0.004XY) \tag{2}$$

where $X$ = geothermal sludge flow rate feeding into a reactor $Y$ = solid % of geothermal sludge $R$ = residence time (hr)

$W$ = wt % of solid loading $SF$ = safety factor

To facilitate the use of Equations (1) and (2) in the economic analyses of waste treatment process from geothermal power plant, a plot was developed where the reactor volume (V) is plotted against residence time and solid loading. In order to calculate the reactor volume for a 50-MW power plant several variables were fixed.

The fixed variables for each system representing different solid loading, residence time, and reactor are: geothermal sludge flow rate 5130 lb/hr, 65% solids in the geothermal sludge, safety factor 1.2, solution density 1.0 g/cm$^3$ and geothermal solid density 2.5 g/cm$^3$. In either system bacterial cultures are stored in 150,000–500,000 gallon tanks while the geothermal sludge is stored in 20,000–60,000 gallon tanks.

TABLE 2

| | Biological Waste Treatment Plant Stream Summary | | | |
|---|---|---|---|---|
| | | Flow Rate | | Amount |
| Stream Number | Description | 10% (W/V) | 20% (W/V) | 30% (W/V) | of Solids |
| 1 | Filter Press Cake from Brine-Solid Separation | 5130 lb/hr | 5130 lb/hr | 5130 lb/hr | 65% |

TABLE 2-continued

Biological Waste Treatment Plant Stream Summary

| Stream Number | Description | Flow Rate 10% (W/V) | Flow Rate 20% (W/V) | Flow Rate 30% (W/V) | Amount of Solids |
|---|---|---|---|---|---|
| 1 | Filter Press Cake from Geothermal Sludge Holding Tank | 5130 lb/hr | 5130 lb/hr | 5130 lb/hr | 65% |
| 2 | Bacteria Culture | 2000 gal/hr | 1000 gal/hr | 615 gal/hr | 0 |
| 3 | Filter Press Recycle | 1785 gal/hr | 785 gal/hr | 450 gal/hr | 0 |
| 4 | Reactor Outlet | 4060 gal/hr | 2080 gal/hr | 1360 gal/hr | |
| 5 | Filter Press Cake | 5130 lb/hr | 5130 lb/hr | 5130 lb/hr | 65% |
| 5 | Filter Press Cake Recycle | 5130 lb/hr | 5130 lb/hr | 5130 lb/hr | ~65% |
| 6 | Filter Press Recycle (Neutralization) | 3685 gal/hr | 1705 gal/hr | 985 gal/hr | 0 |
| 7 | Water and Nutrients | 2000 gal/hr | 1000 gal/hr | 615 gal/hr | 0 |
| 8 | Soda Ash | 400 lb/hr | 400 lb/hr | 400 lb/hr | 100% |
| 9 | Reinjection Liquid | 3730 gal/hr | 1740 gal/hr | 1020 gal/hr | 0 |
| 10 | Precipitated Solid | <100 lb/hr | <100 lb/hr | <100 lb/hr | 65% |
| 11 | Neutralization Exit | 3730 gal/hr | 1750 gal/hr | 1030 gal/hr | 0 |

The total capital cost of each treatment plant was amortized over a 10-year plant life at an interest rate of 10% which is to be paid in ten equal end-of-year payments. The annual operating cost of each process, including nutrient costs for the bacterial culture, disposal costs of solids, electric power, irrigation water, insurance, labor, and pH control, ranged from $710,000 to $930,000. The total annual cost of each process (amortized capital plus annual operating costs) ranges from approximately $1.27 million to $1.63 million. This indicates that the subject process is commercially feasible.

FIG. 1 shows a typical set up having five quality control stations. At station A the growth of microorganisms is monitored. Since the types of organisms used in these processes are initially grown separately, two separate fermentors are used. Incoming sludge station B is monitored routinely for pH, metal species, and concentration to allow for programming of the following steps. At station C, mixing temperature, oxygen, and pH should also be monitored routinely. At Stations C and D, two important aspects of the process have to analyzed for. At C, the amount of metal(s) removed from the sludge is monitored while at D the concentration of metal(s) in the solution is determined. C determines the efficiency of the process and D in addition to the total metal concentration, determines the minimum inhibitory concentration (MIC) of the metal. This is the concentration of the metal which decreases the efficiency of the microorganisms and indicates the need for fresh biomass and nutrients. Recycling option at this stage may not be advisable for two reasons: (i) MIC and (ii) the nature of the biochemical mechanism on which the process is based. In the overall biochemical process, the microorganisms are attached to a substrate, (geothermal sludge) and therefore, most of the biomass will be associated with the filter cake. The recycling option, however, is justifiable if MIC has not been reached and if a single cycle was incomplete. Stations E, F, and D monitor metal recovery and the quality of the water used for reinjection and/or irrigation.

Figure 2:
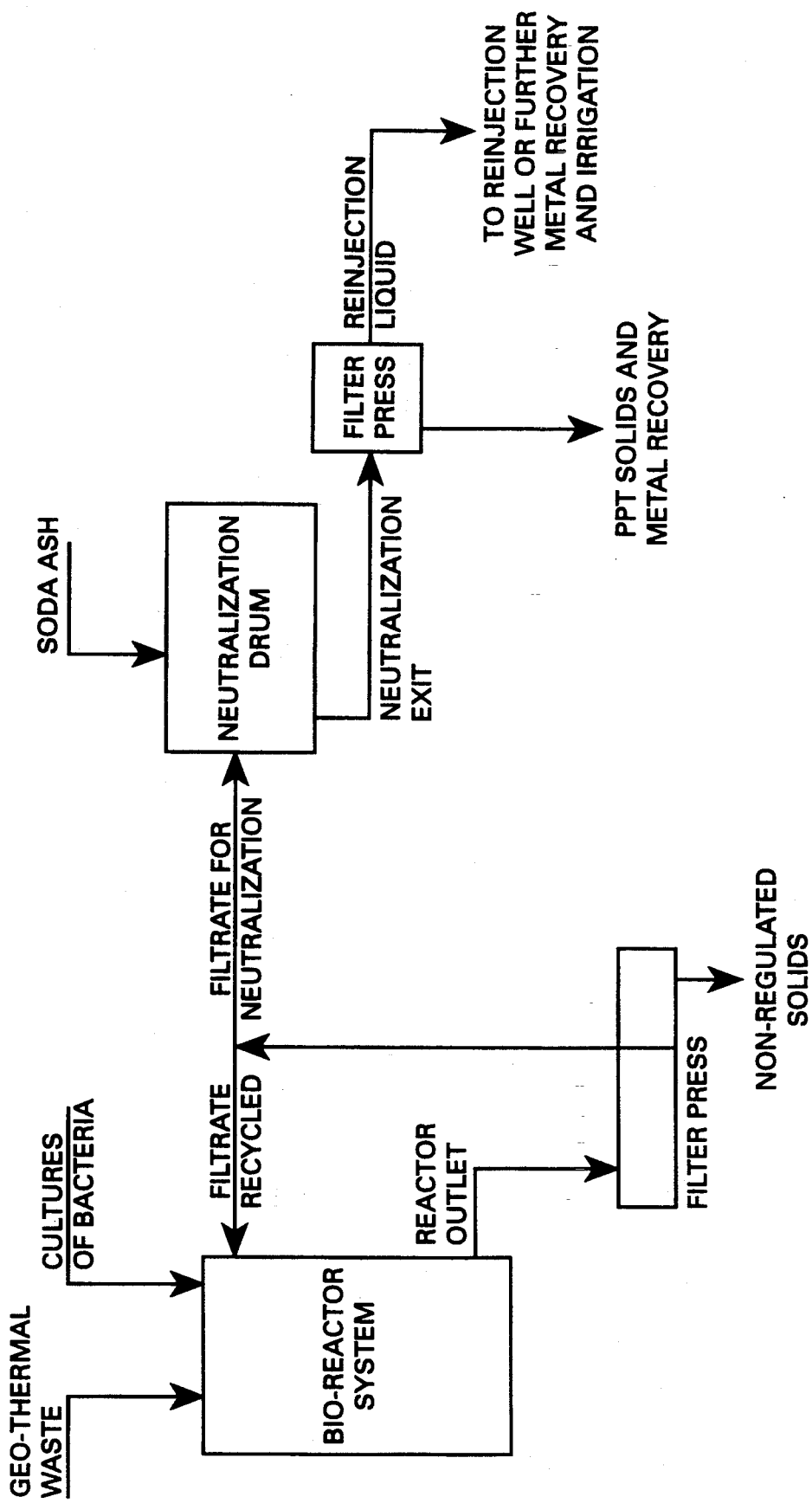
FIG. 2 illustrates a process flow diagram for the subject biotechnology.

To emphasize the importance of optimization and corresponding process modifications, the effect of a temperature of 55° C., pH 1-2 and sludge concentrations of 10%, 20%, 30%, and 40% will be briefly discussed. For the sake of brevity, only examples of copper and manganese will be discussed. The rates of removal of these two metals at the elevated temperature and pH 1-2 demonstrate that highly efficient rates of metal removal can be achieved. The use of Thiobacillus mutants selected for their ability to effectively metabolize metal sulfides at high (55° C.) temperatures is a major advance provided by the subject invention. Further modifications, such as in the case of manganese, should lead to a better than 80% demineralization in a 24 hour treatment interval. Of particular interest is that at elevated temperature there is very little difference between the efficiency of agitated tank and fluidized bed. This has important implications, for example, in terms of air compressors needed for sludge concentrations of 40%. FIG. 2 shows a process flow diagram which incorporates the subject methodology. Elevated temperatures and acidic pH necessitate consideration of corrosive resistant materials which may be used in the construction and/or lining of holding vessels and tanks.

Figure 3:
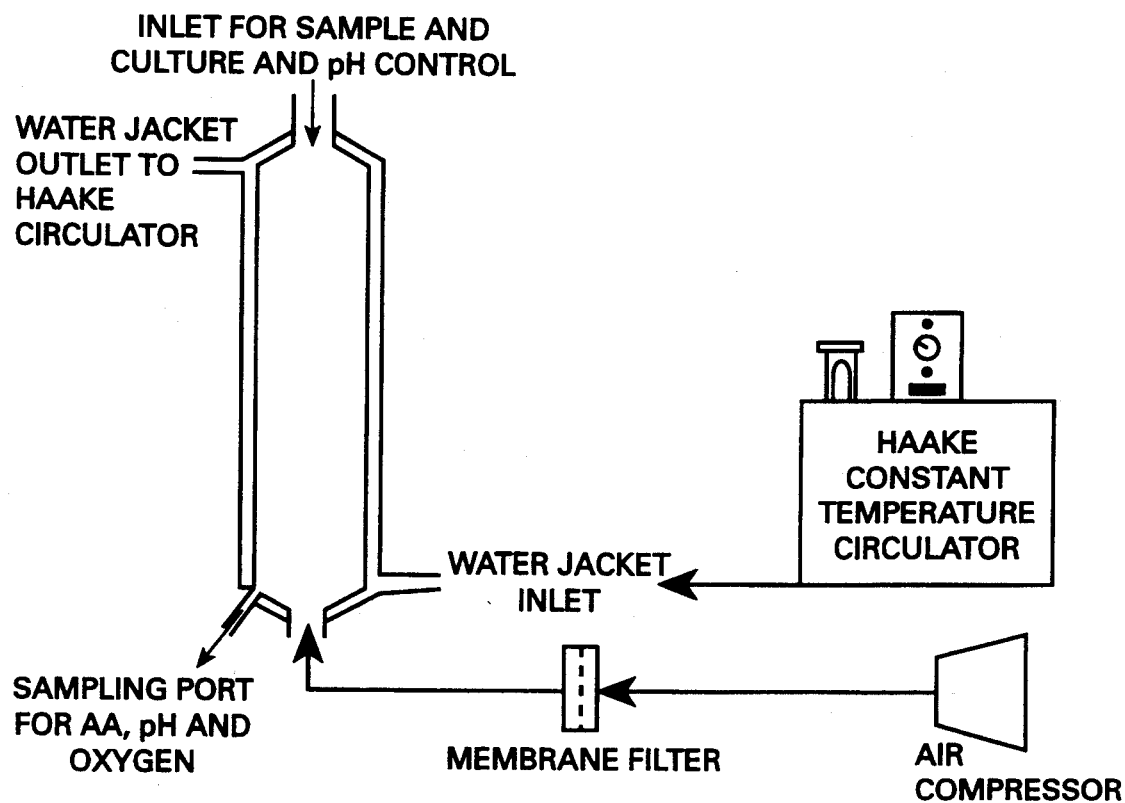
FIG. 3 shows schematized all glass fluidized bed bioreactor.
Figure 4:
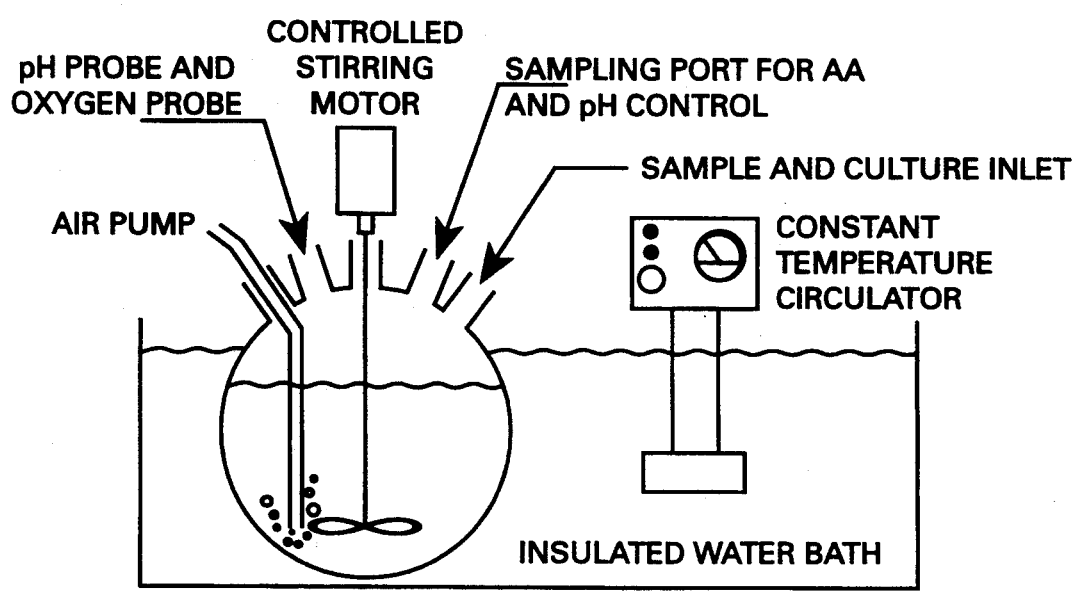
FIG. 4 shows schematized all glass agitated tank bioreactor.

The following experiments were carried out in smaller, all glass bioreactors as shown in FIGS. 3 and 4. Both reactors are based on a three liter capacity. The fluidized bed bioreactor (FIG. 3) was heated by a hot water jacket, while the agitated tank bioreactor (FIG. 4) was heated by means of a water bath. In temperature was controlled and maintained at 55° C., with temperature and pressure monitored during the course of reactions (some data from Premuzic, E. T., et al., *Geothermal Program Review IX Proceedings*, pp. 77–84 (Mar. 19–21, 1991), the contents of which is hereby incorporated by reference, is described herein).

Figure 5A:
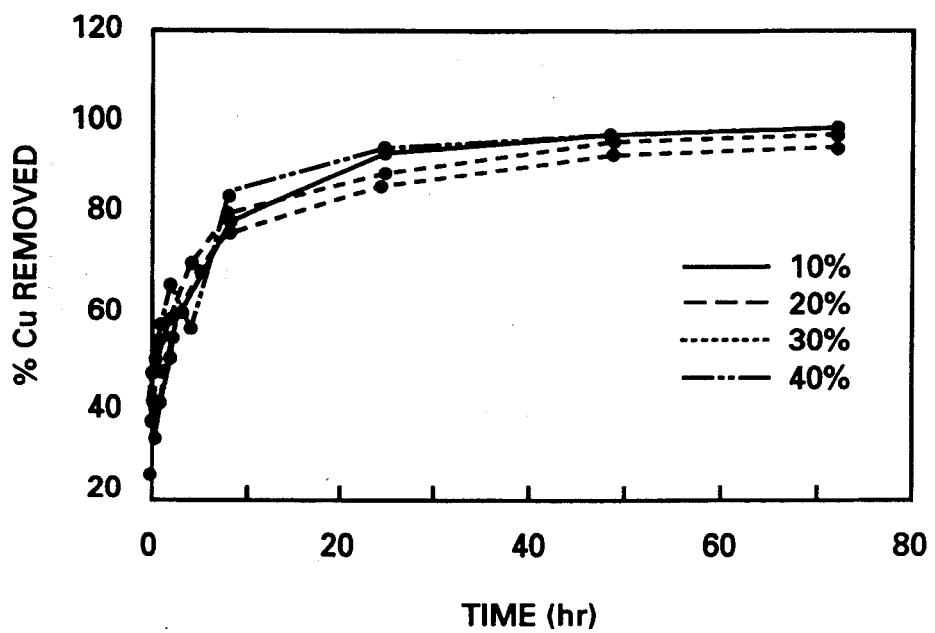
FIG. 5A graphically depicts removal of copper from a geothermal residual sludge solid phase in an agitated tank bioreactor at 55° C. over a period of 72 hours.
Figure 5B:
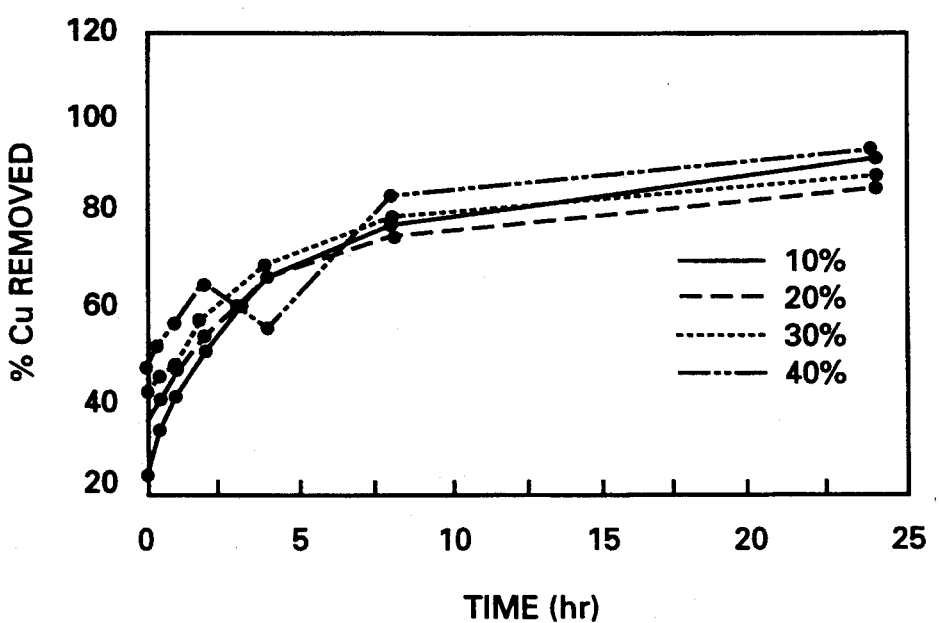
FIG. 5B graphically depicts removal of copper from a geothermal residual sludge solid phase in an agitated tank bioreactor at 55° C. over a period of 24 hours.
Figure 6A:
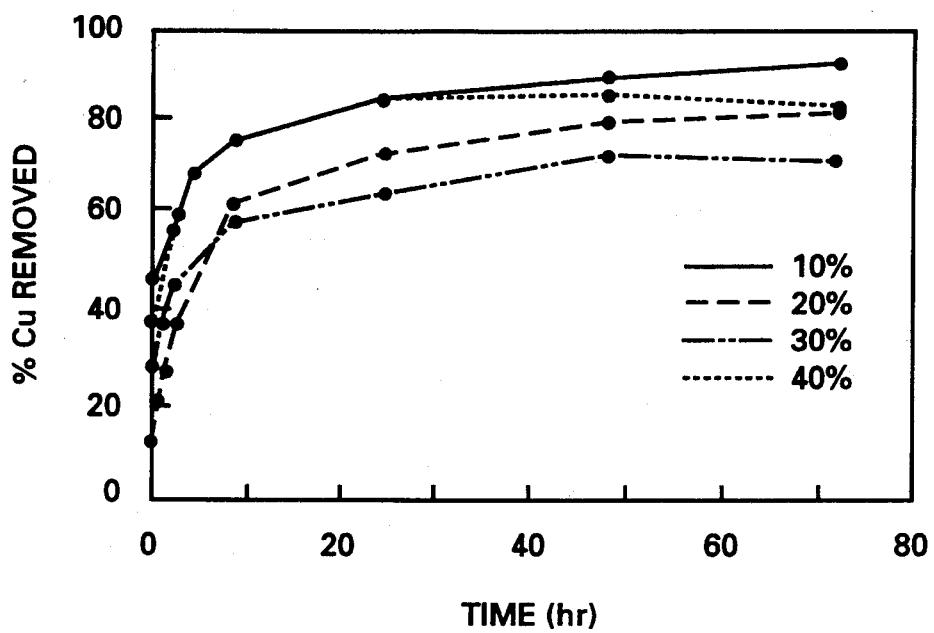
FIG. 6A graphically illustrates removal of copper from a geothermal residue sludge solid phase in a fluidized bed bioreactor at 55° C. over 72 hours.
Figure 6B:
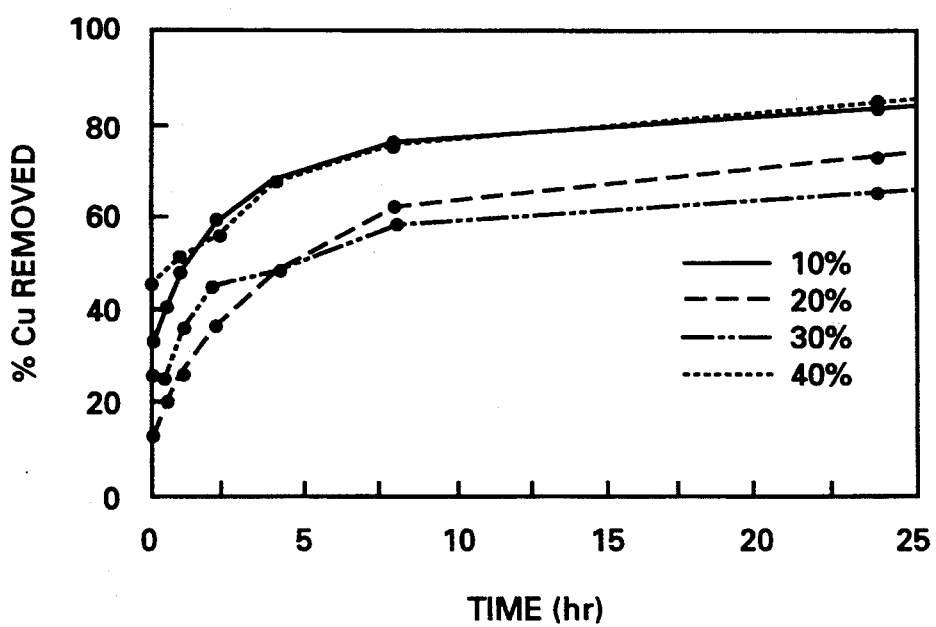
FIG. 6B graphically illustrates removal of copper from a geothermal residue sludge solid phase in a fluidized bed bioreactor at 55° C. over 24 hours.
Figure 7A:
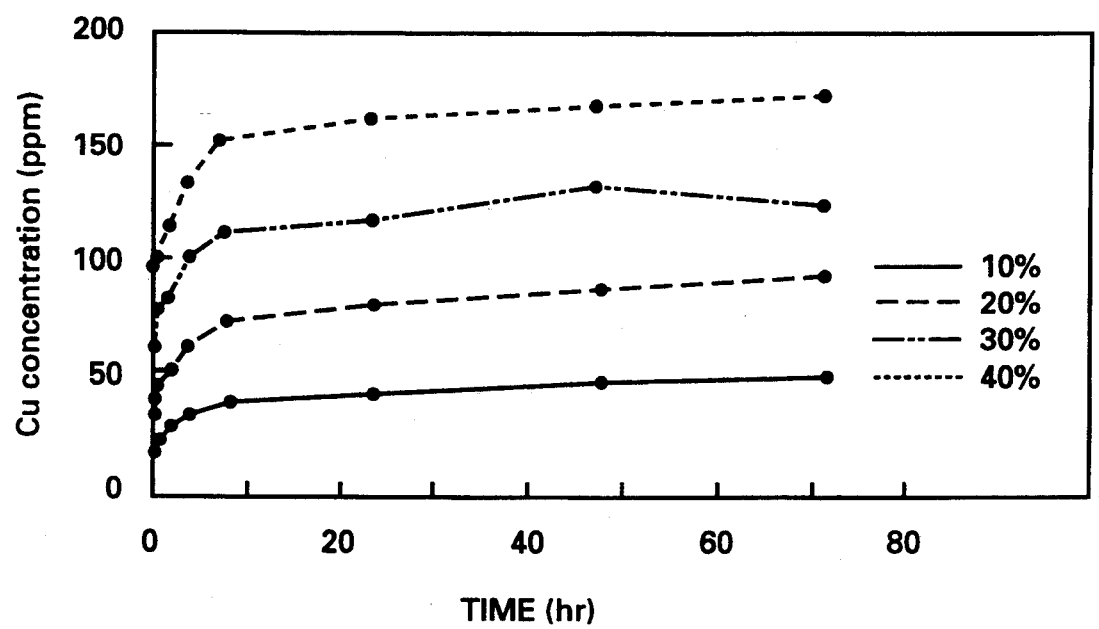
FIG. 7A graphically shows the change in copper concentration in the liquid phase after biotreatment of the sludge solid phase in an agitated tank bioreactor at 55° C. over a 72 hour period.
Figure 7B:
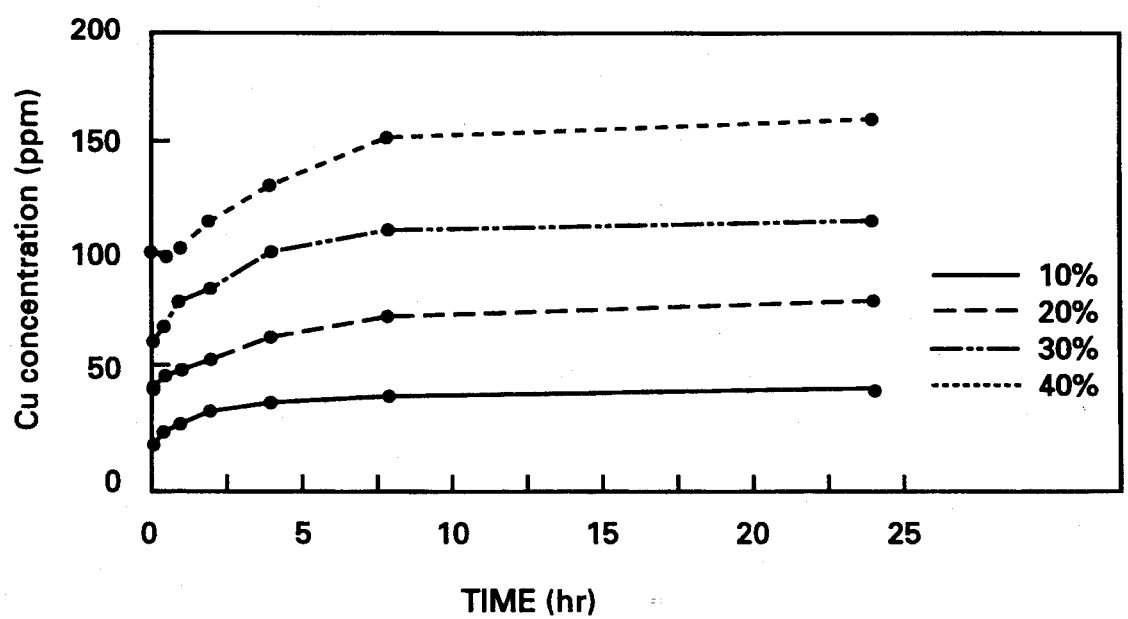
FIG. 7B graphically shows the change in copper concentration in the liquid phase after biotreatment of the sludge solid phase in an agitated tank bioreactor at 55° C. over a 24 hour period.
Figure 8A:
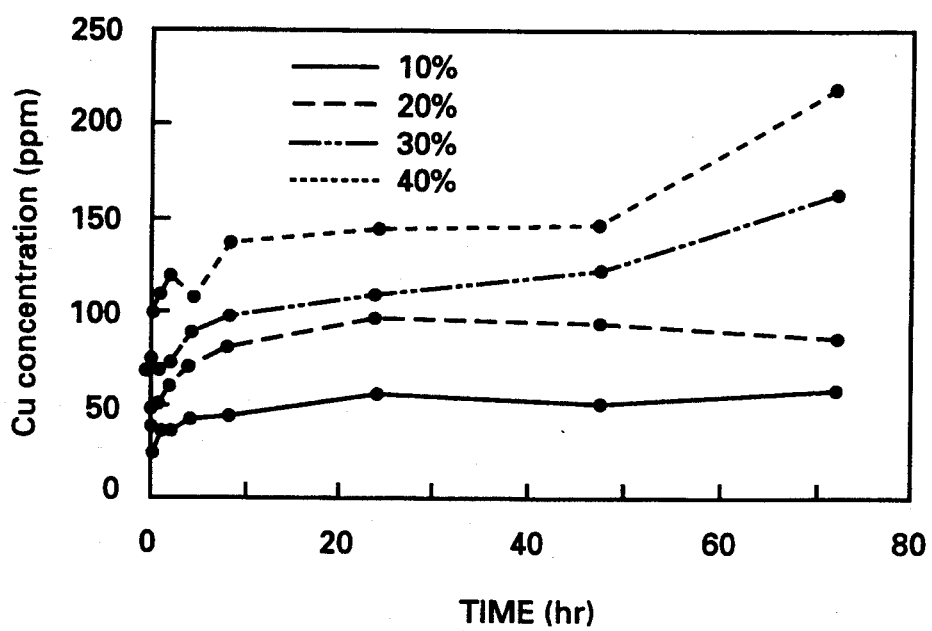
FIG. 8A graphically shows the change in copper concentration in the liquid phase after biotreatment of the sludge solid phase in a fluidized bed bioreactor at 55° C. over a 72 hour period.
Figure 8B:
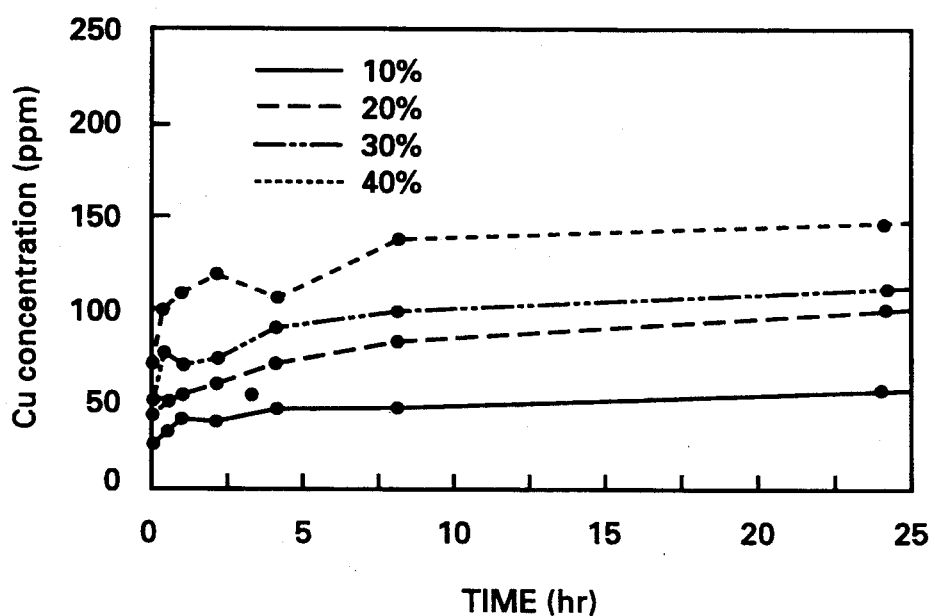
FIG. 8B graphically shows the change in copper concentration in the liquid phase after biotreatment of the sludge solid phase in a fluidized bed bioreactor at 55° C. over a 24 hour period.
Figure 9A:
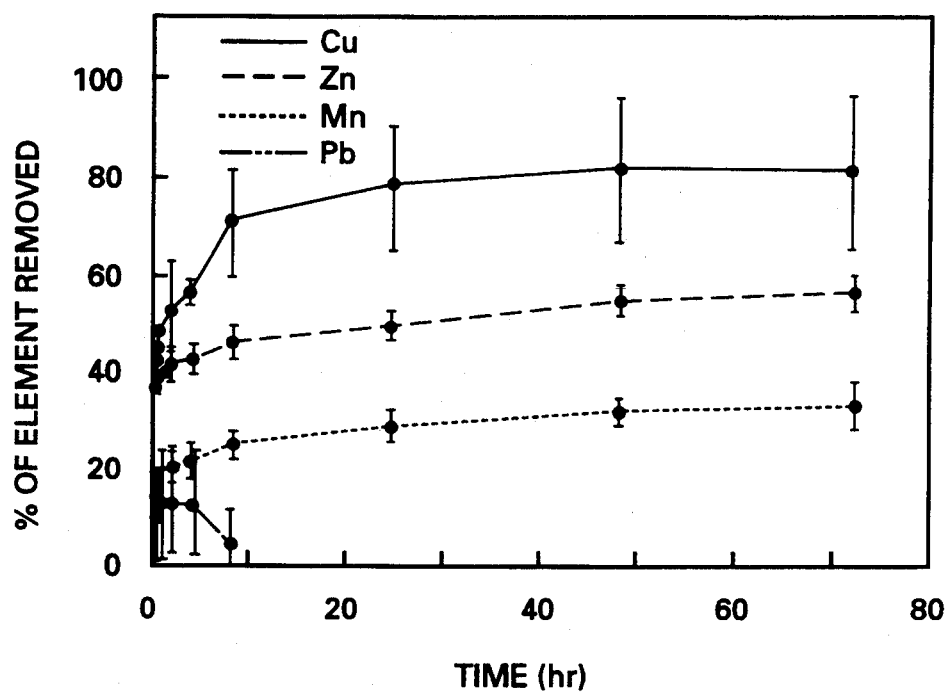
FIG. 9A graphically illustrates removal of copper, zinc, manganese and lead in an agitated tank bioreactor at 55° C. and 40% slurry loading over a 72 hour period.
Figure 9B:
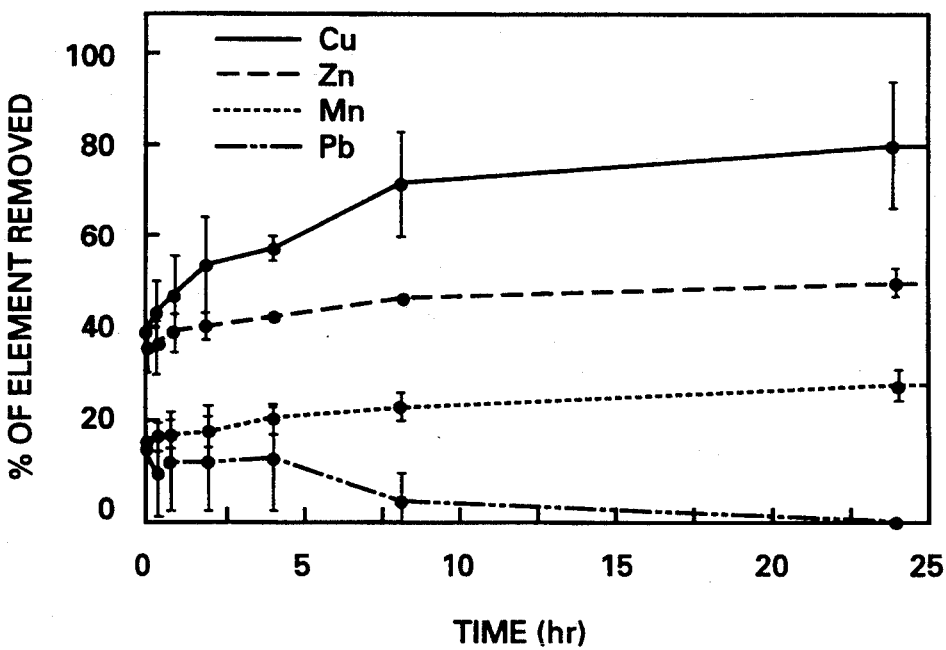
FIG. 9B graphically illustrates removal of copper, zinc, manganese and lead in an agitated tank bioreactor at 55° C. and 40% slurry loading over a 24 hour period.
Figure 10A:
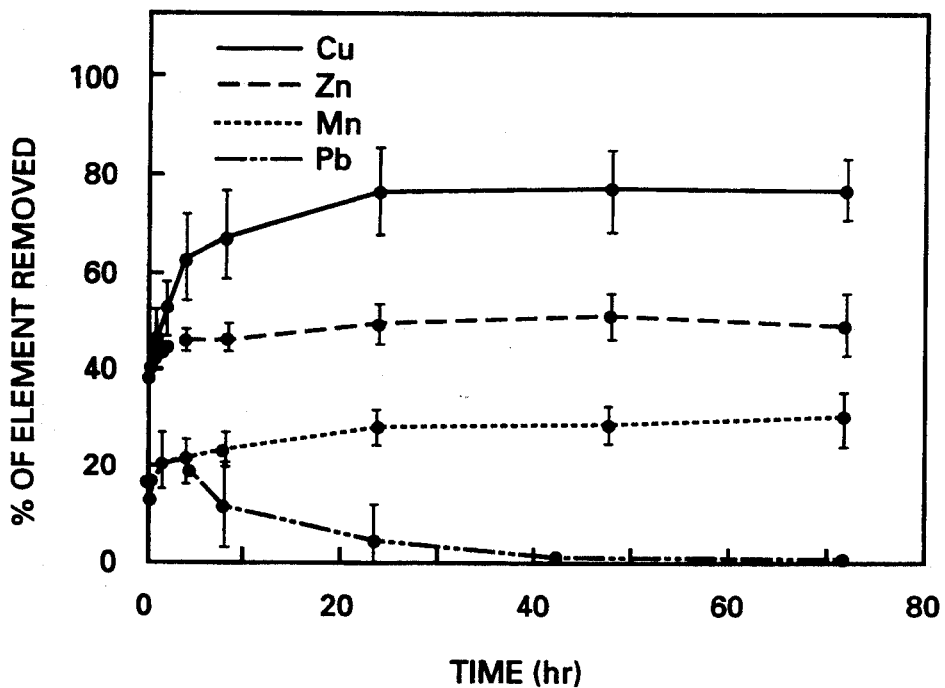
FIG. 10A graphically illustrates removal of copper, zinc, manganese and lead in an agitated tank fluidized bed bioreactor at 55° C. and 40% slurry loading over a 72 hour period.
Figure 10B:
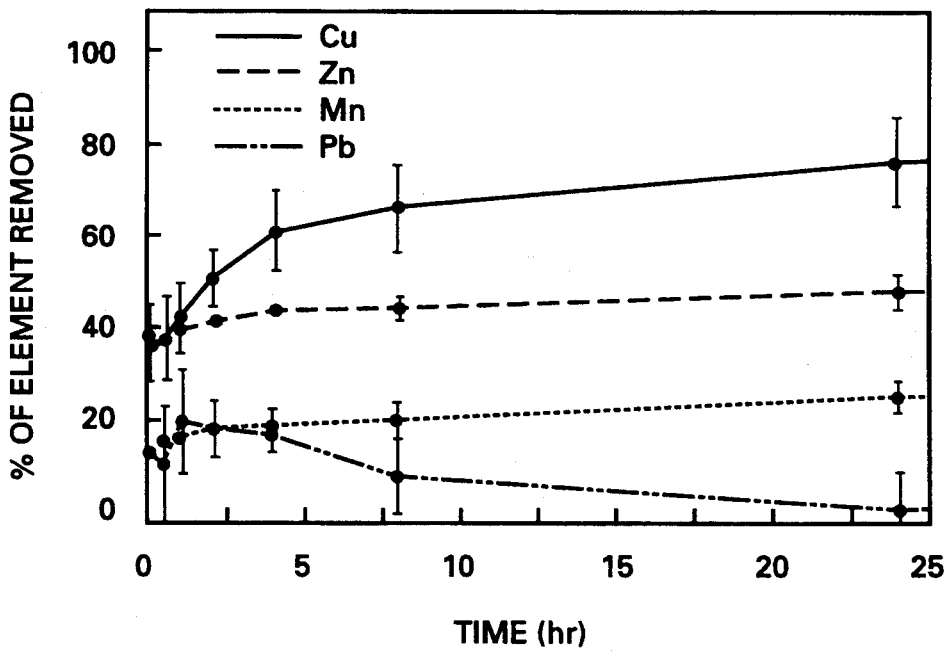
FIG. 10B graphically illustrates removal of copper, zinc, manganese and lead in an agitated tank fluidized bed bioreactor at 55° C. and 40% slurry loading over a 24 hour period.
Figure 11:
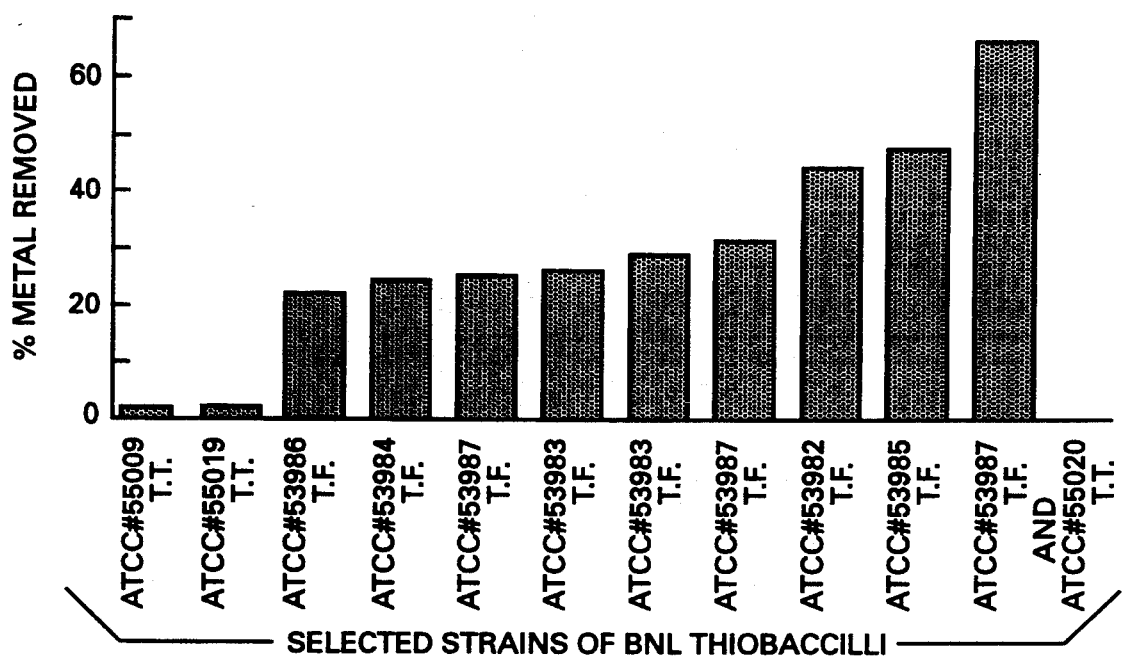
FIG. 11 graphically illustrates the removal of Cr from residual brine sludge BR-1 after five days exposure to various strains of *Thiobacillus ferrooxidans* and *Thiobacillus thiooxidans* at 25° C.
Figure 12:
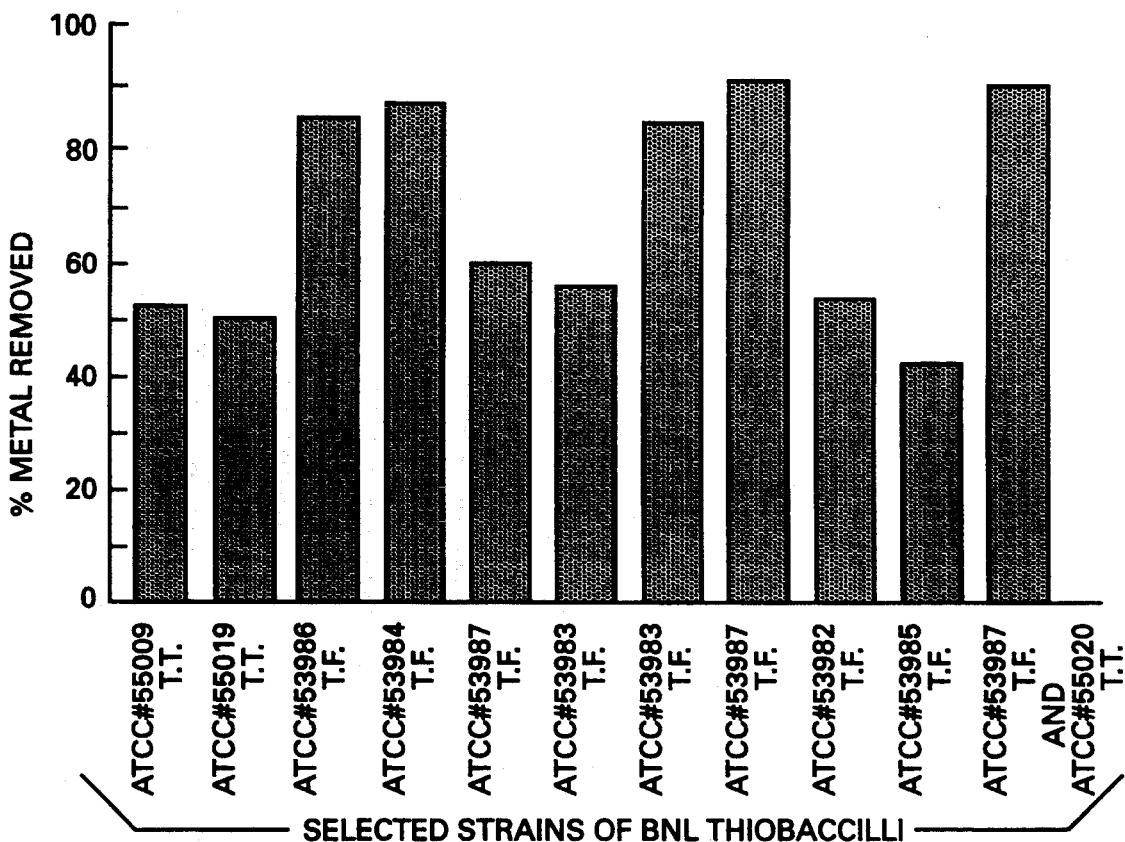
FIG. 12 graphically illustrates the removal of Cu from residual brine sludge BR-1 after five days exposure to various strains of *Thiobacillus ferrooxidans* and *Thiobacillus thiooxidans* at 25° C.
Figure 13:
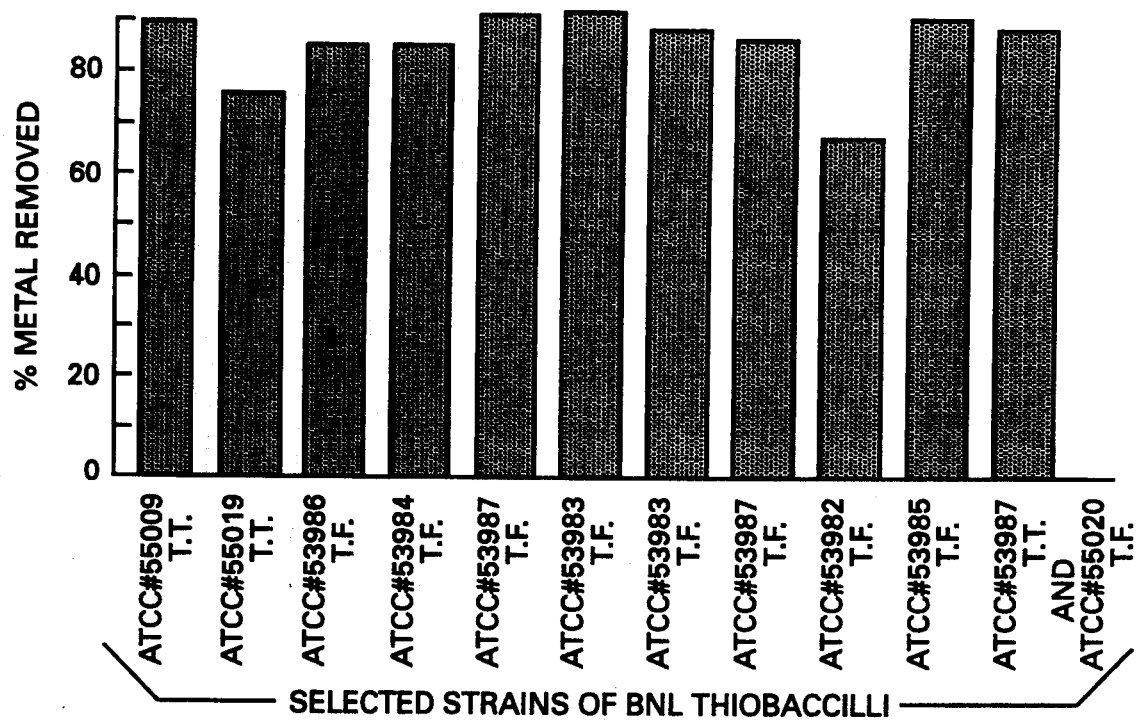
FIG. 13 graphically illustrates the removal of Zn from residual brine sludge BR-1 after five days exposure to various strains of *Thiobacillus ferrooxidans* and *Thiobacillus thiooxidans* at 25° C.
Figure 14:
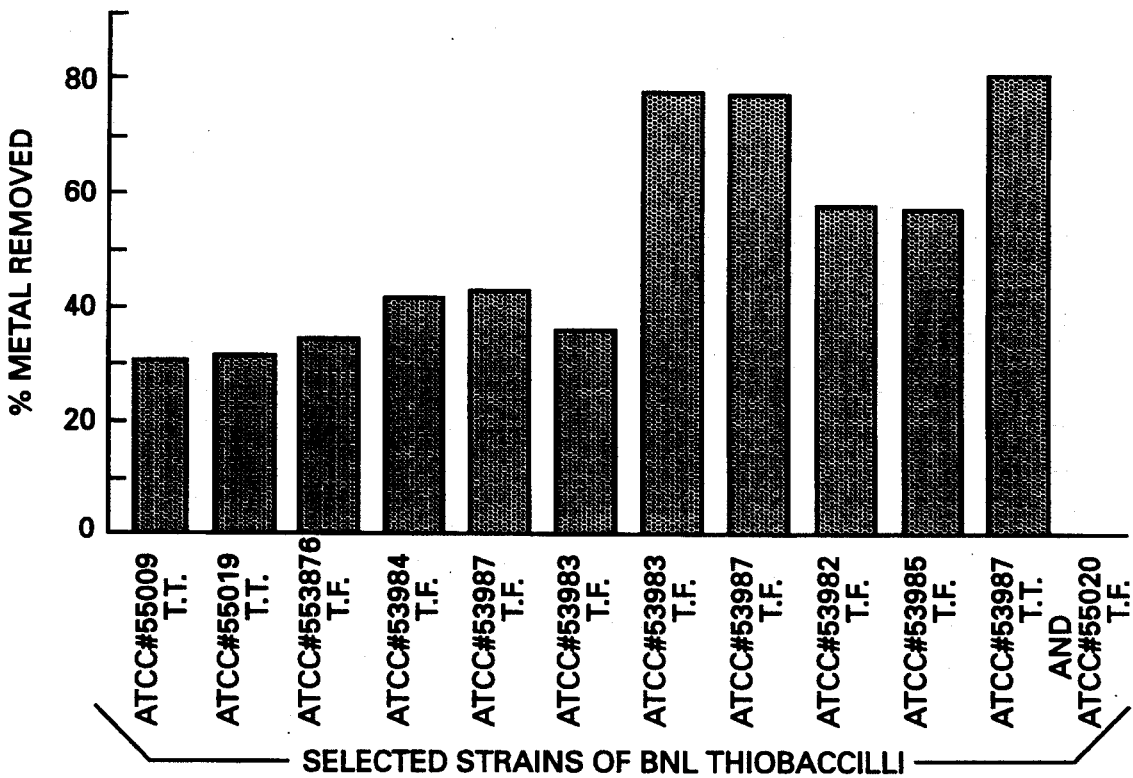
FIG. 14 graphically illustrates the removal of Mn from residual brine sludge BR-1 after five days exposure to various strains of *Thiobacillus ferrooxidans* and *Thiobacillus thioxidans* at 25° C.
Figure 15:
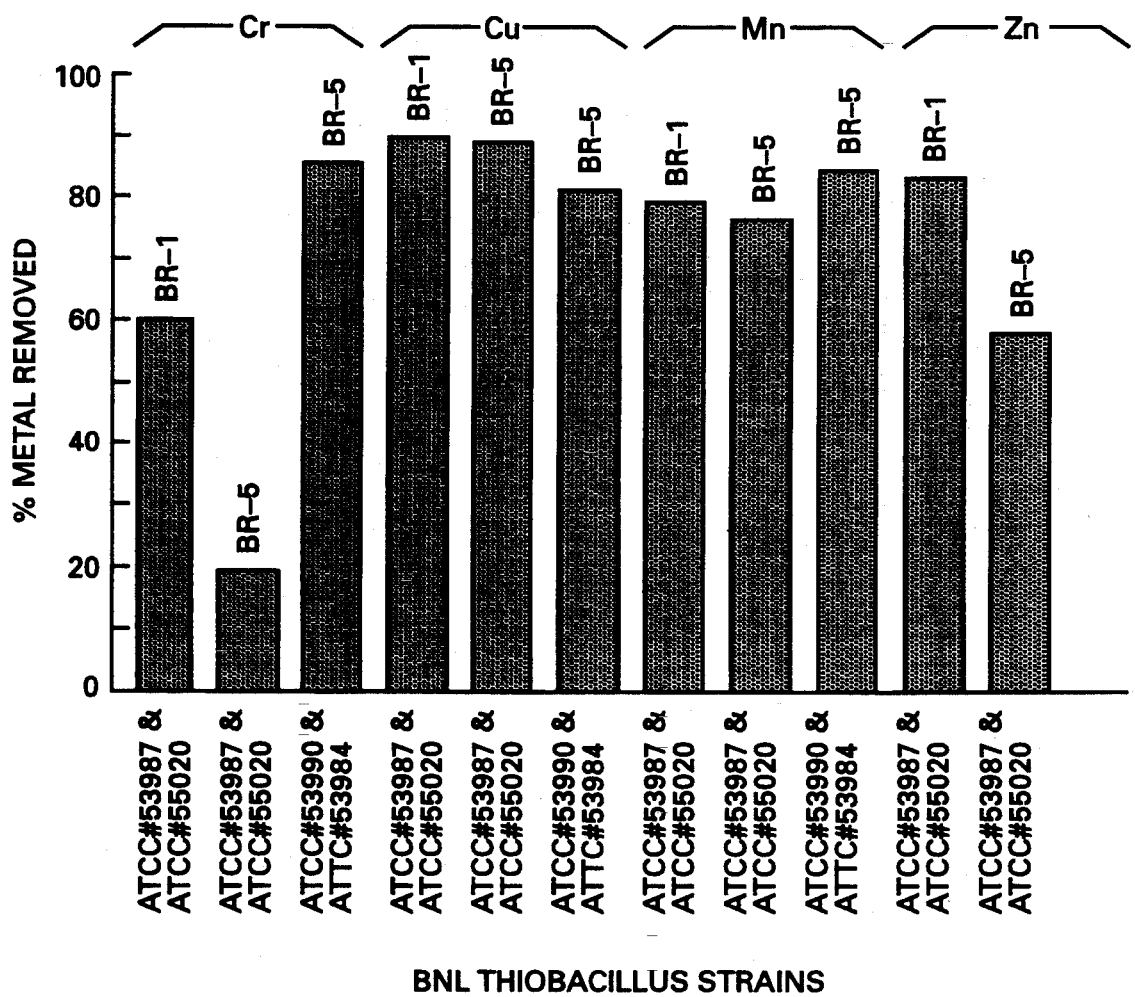
FIG. 15 graphically illustrates the removal of Cr, Cu, Mn and Zn from residual brine sludges BR-1 and BR-5 after five days exposure to mixed cultures of *Thiobacillus thioxidans* and *Thiobacillus ferroxidans* at 25° C.
Figure 16:
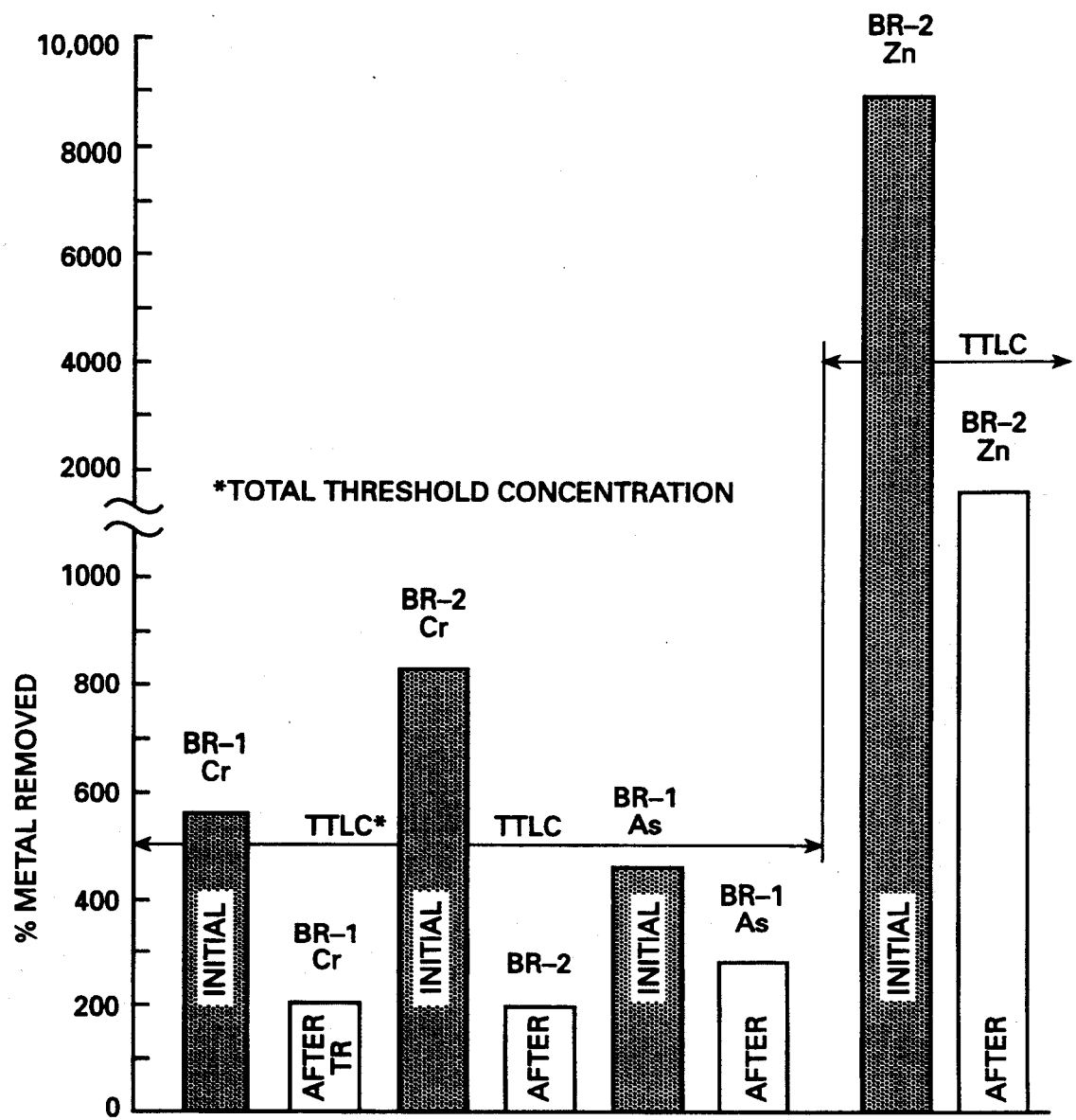
FIG. 16 graphically illustrates the removal of metals from residual brine sludges BR-1 and BR-2 five days exposure to various strains of at 25° C. *Thiobacillus ferroxidans* and *Thiobacillus thioxidans* and illustrates the ability of the present invention to reduce the levels of toxic metals to the TTLC within a five-day period.
Figure 17A:
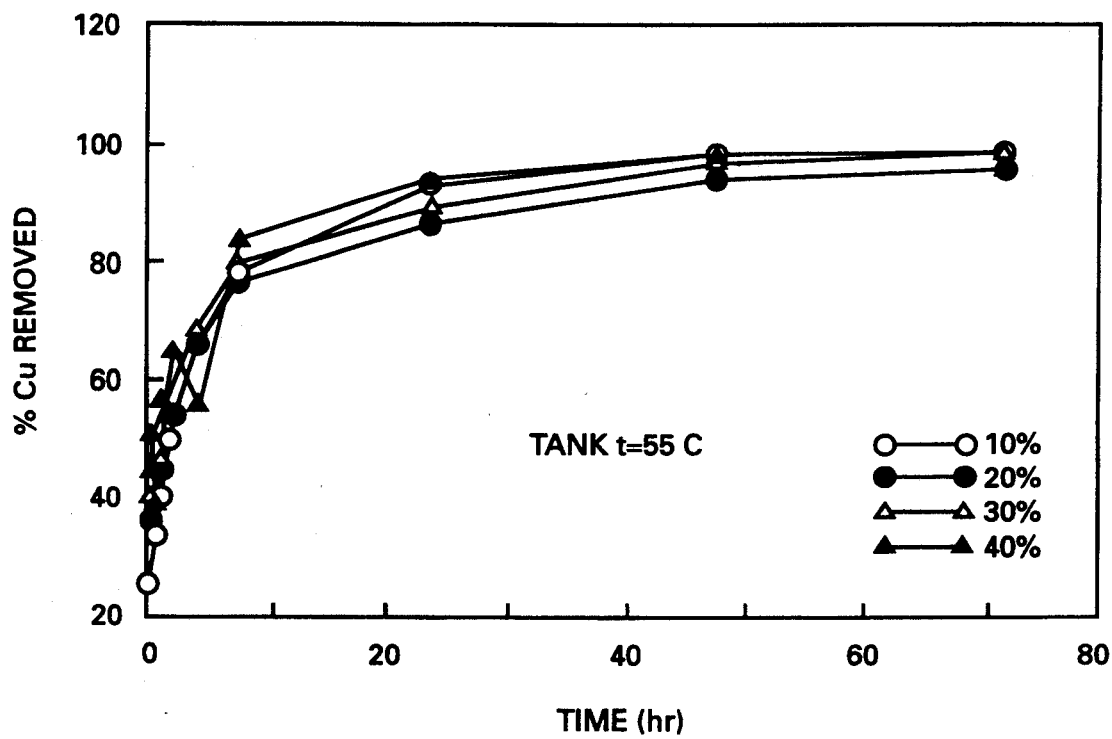
FIG. 17A graphically illustrates the removal of Cu from a residual brine in an agitated tank bioreactor at 55° C. over a period of 72 hrs.
Figure 17B:
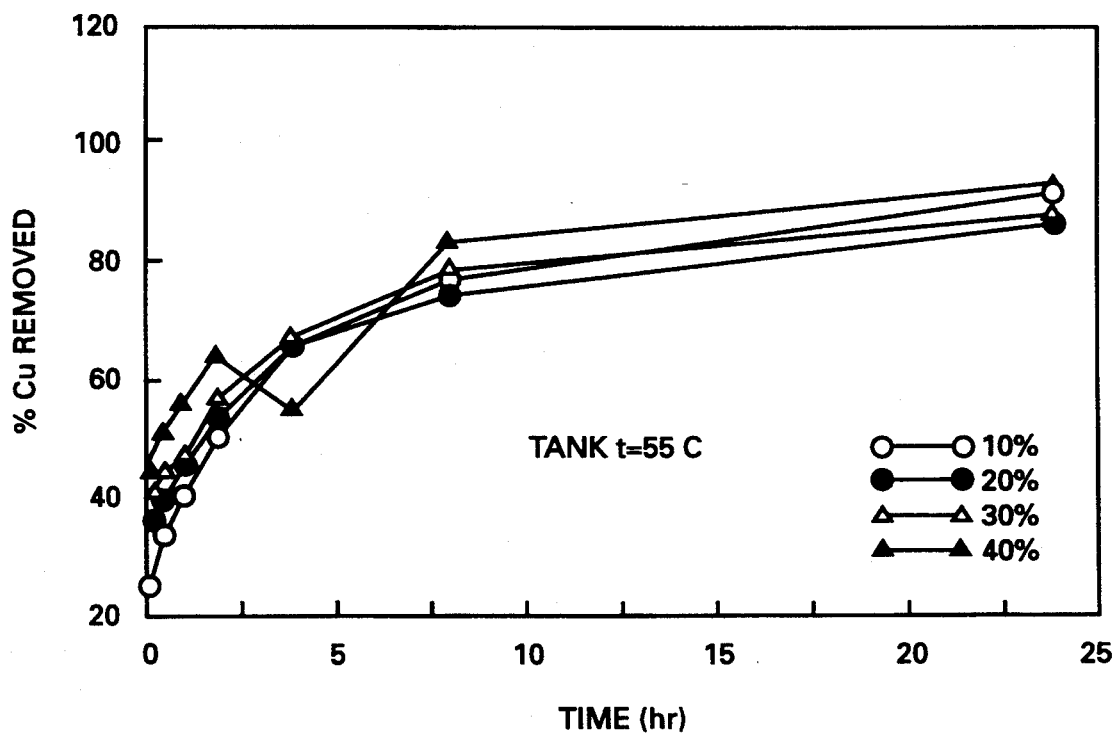
FIG. 17B graphically illustrates the removal of Cu from a residual brine in an agitated tank bioreactor at 55° C. over a period of 24 hrs.
Figure 18A:
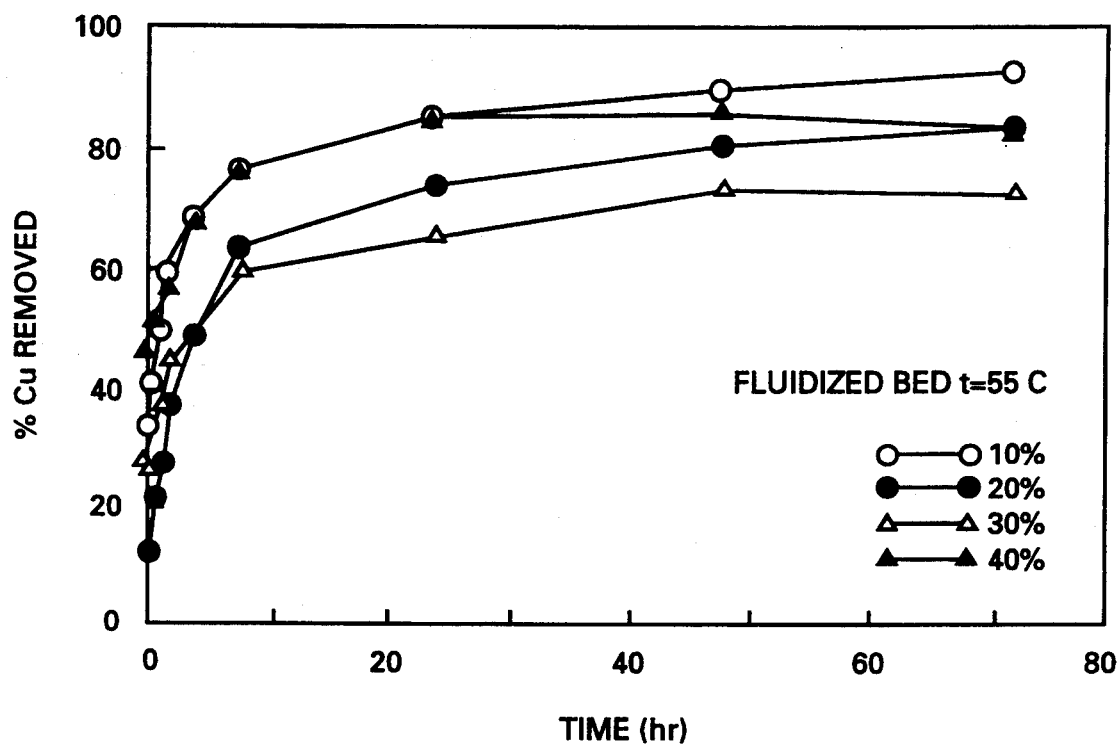
FIG. 18A graphically illustrates the removal of Cu from a residual brine in a fluidized bed at 55° C. over a period of 72 hrs.
Figure 18B:
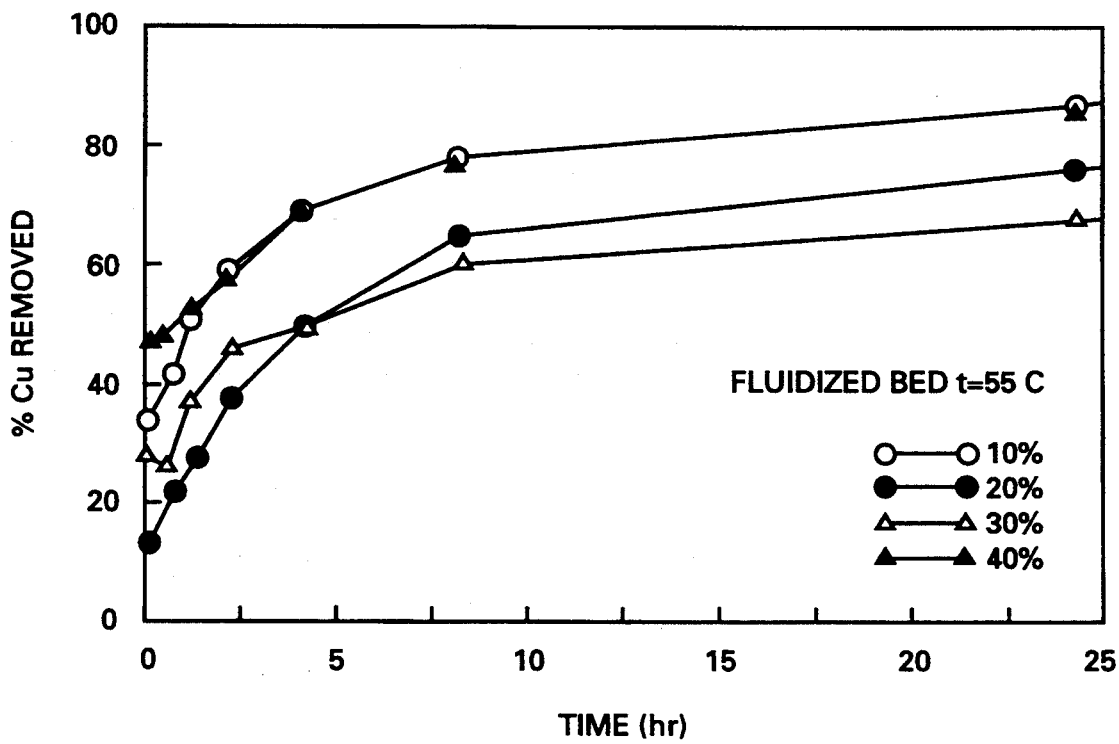
FIG. 18B graphically illustrates the removal of Cu from a residual brine in a fluidized bed at 55° C. over a period of 24 hrs.
Figure 19A:
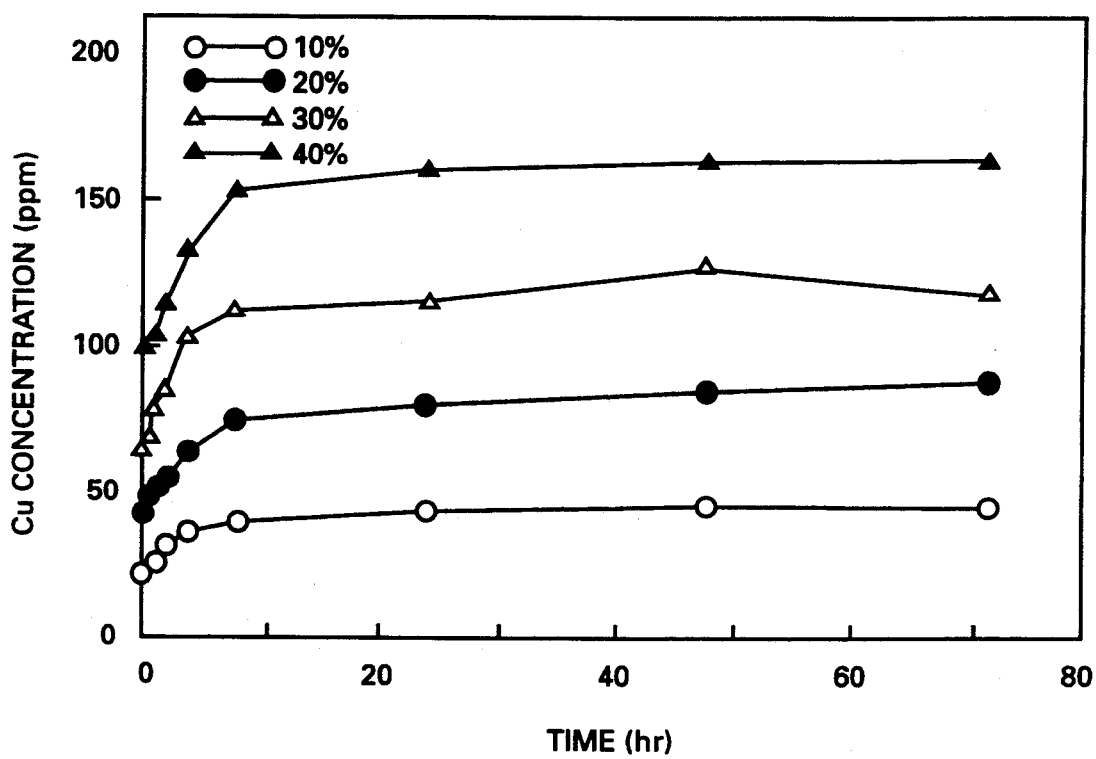
FIG. 19A graphically illustrates the change in copper concentration after biotreatment of a residual brine in an agitated tank bioreactor at 55° C. over a 72 hour period.
Figure 19B:
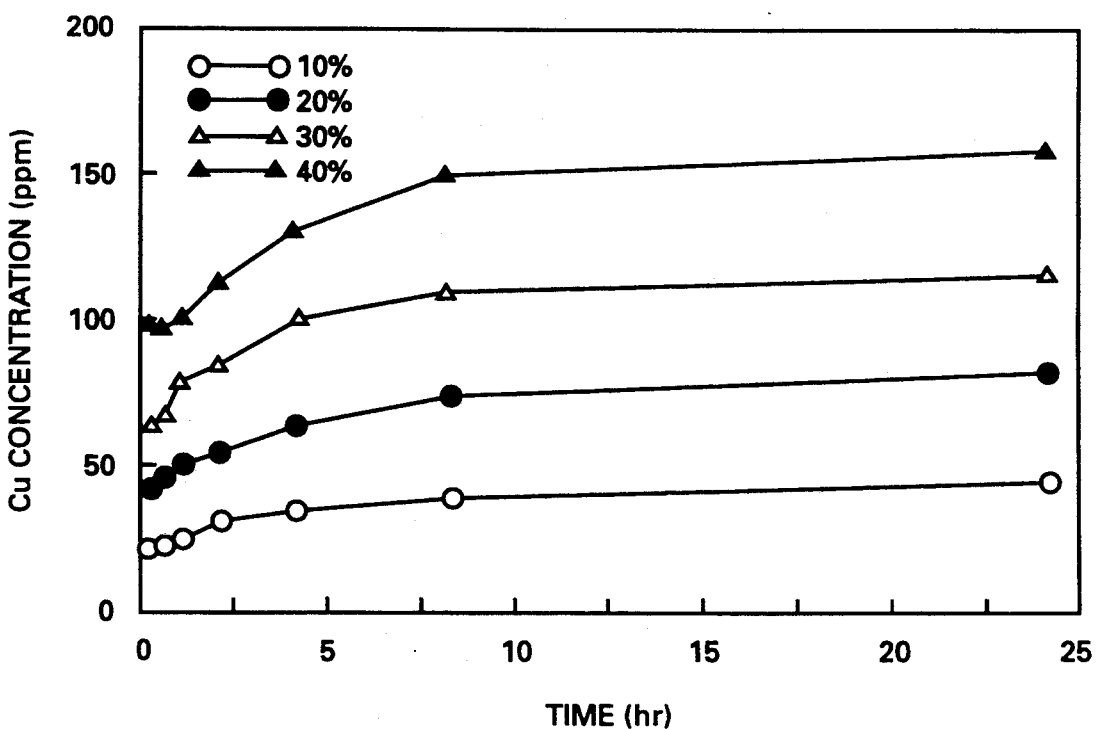
FIG. 19B graphically illustrates the change in copper concentration after biotreatment of a residual brine in an agitated tank bioreactor at 55° C. over a 24 hour period.
Figure 20A:
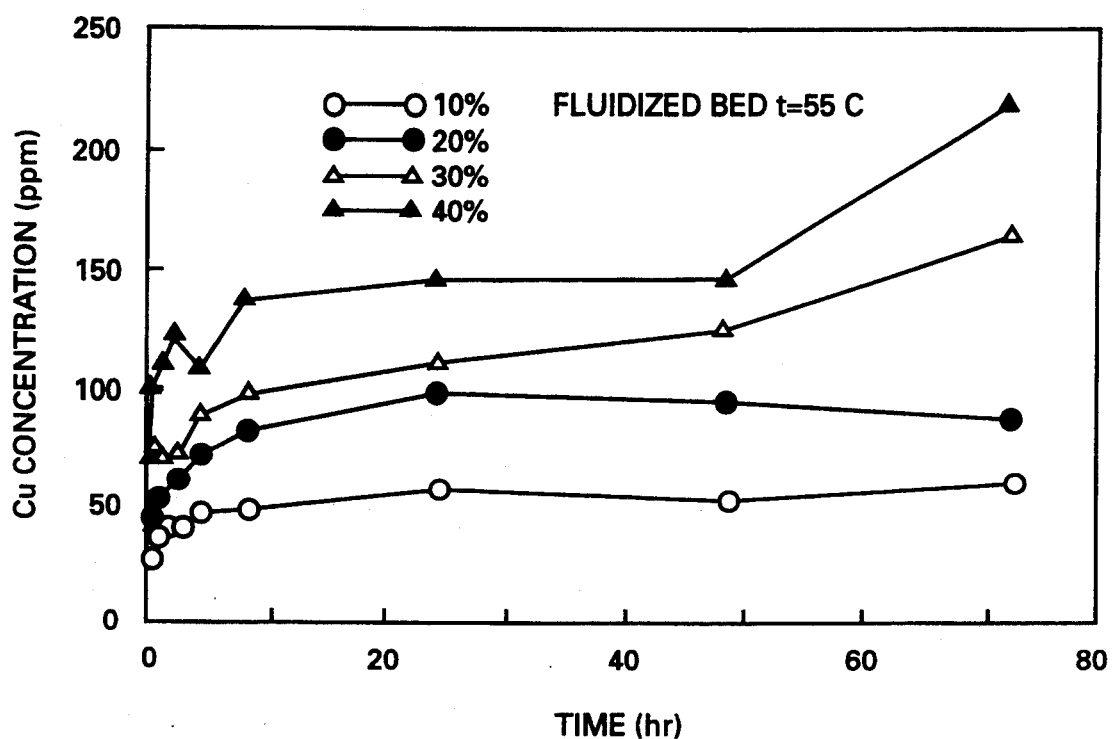
FIG. 20A graphically illustrates the change in copper concentration after biotreatment of a residual brine in a fluidized bed at 55° C. over a 72 hour period.
Figure 20B:
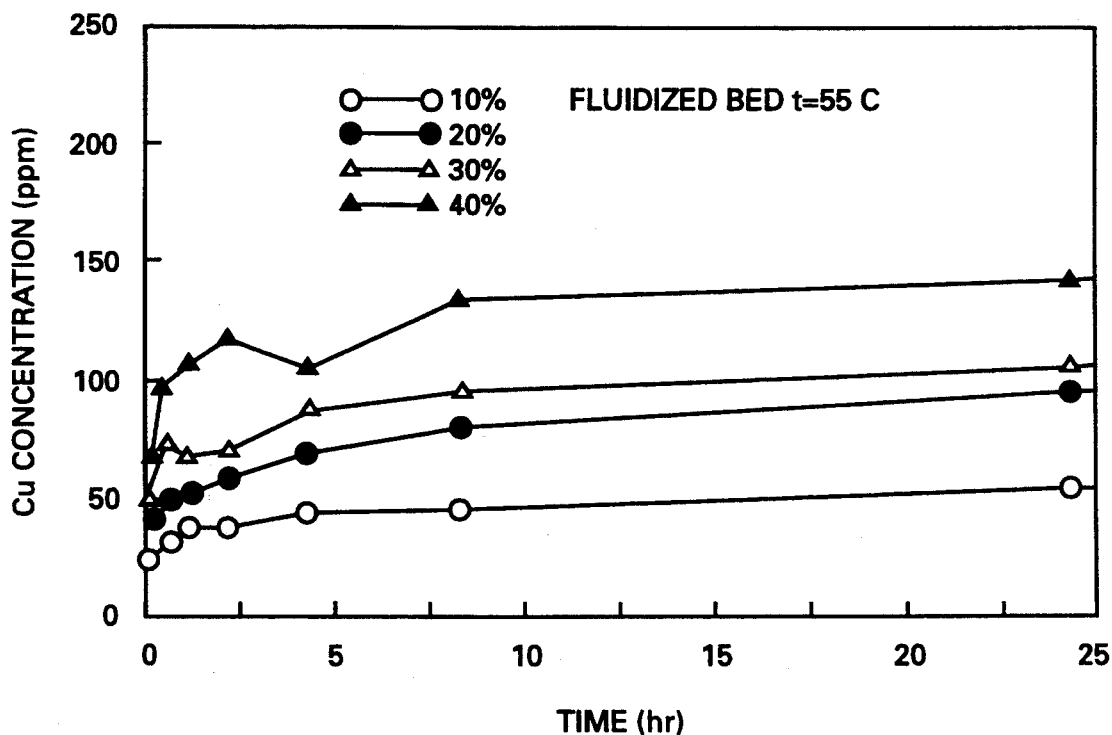
FIG. 20B graphically illustrates the change in copper concentration after biotreatment of a residual brine in a fluidized bed at 55° C. over a 24 hour period.
Figure 21A:
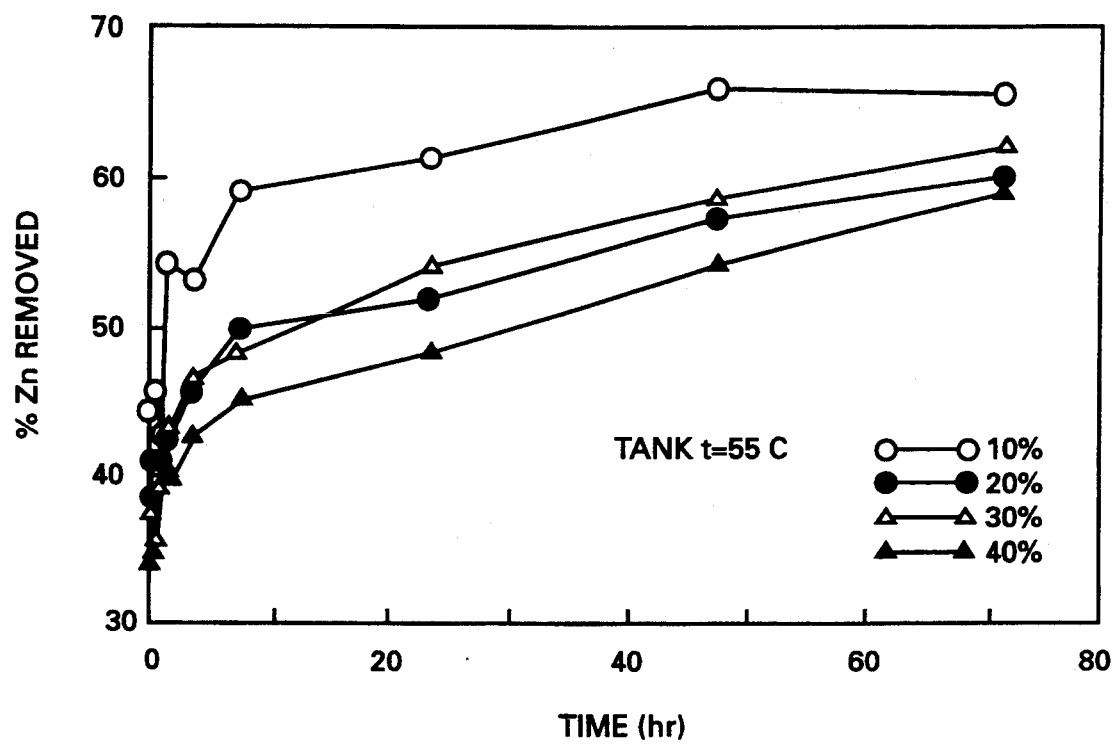
FIG. 21A graphically illustrates the removal of Zn from a residual brine in an agitated tank bioreactor at 55° C. over a period of 72 hrs.
Figure 21B:
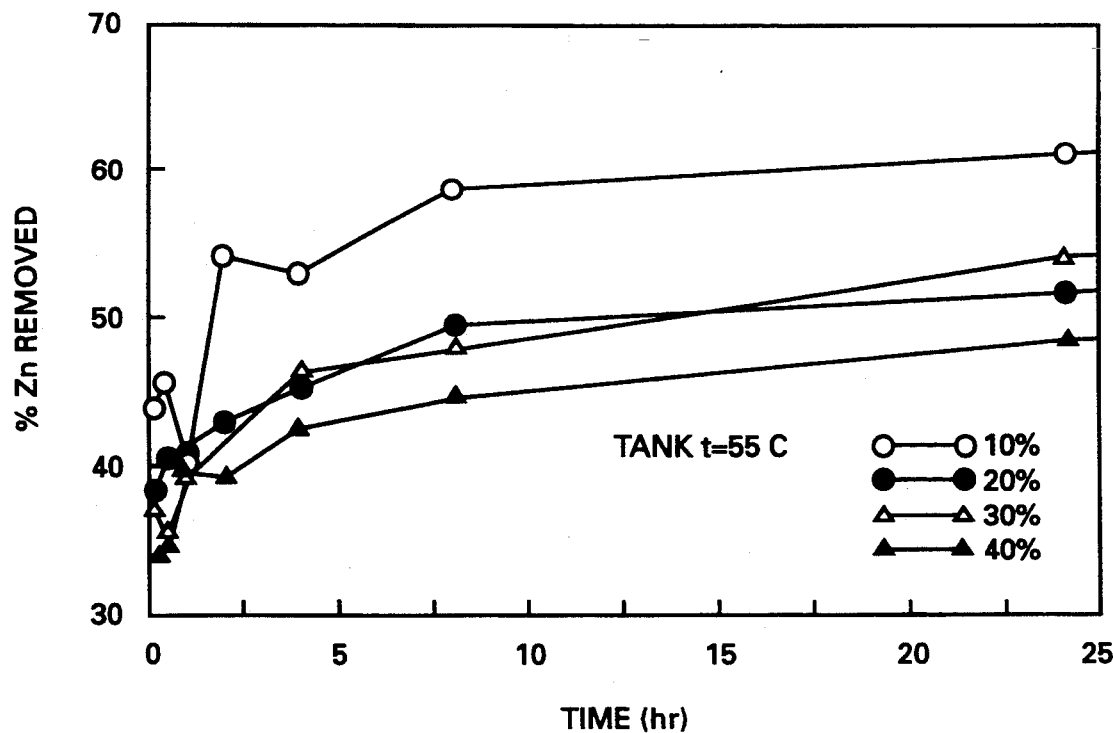
FIG. 21B graphically illustrates the removal of Zn from a residual brine in an agitated tank bioreactor at 55° C. over a period of 24 hrs.
Figure 22A:
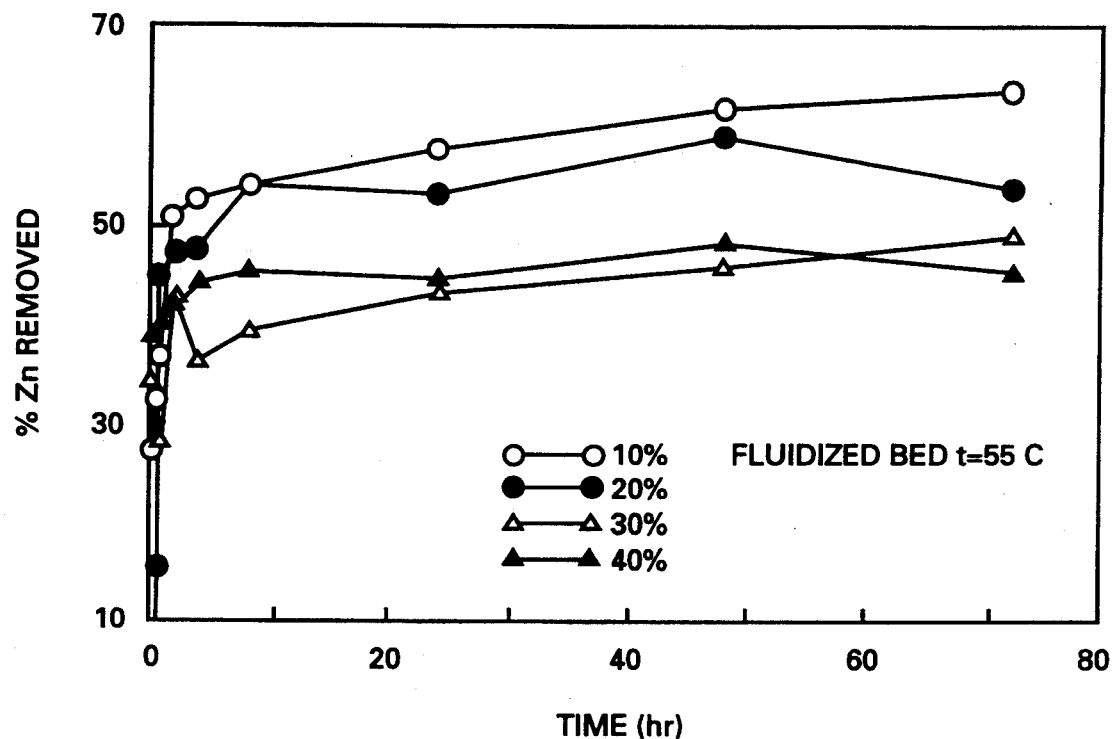
FIG. 22A graphically illustrates the removal of Zn from a residual brine in a fluidized bed at 55° C. over a period of 72 hrs.
Figure 22B:
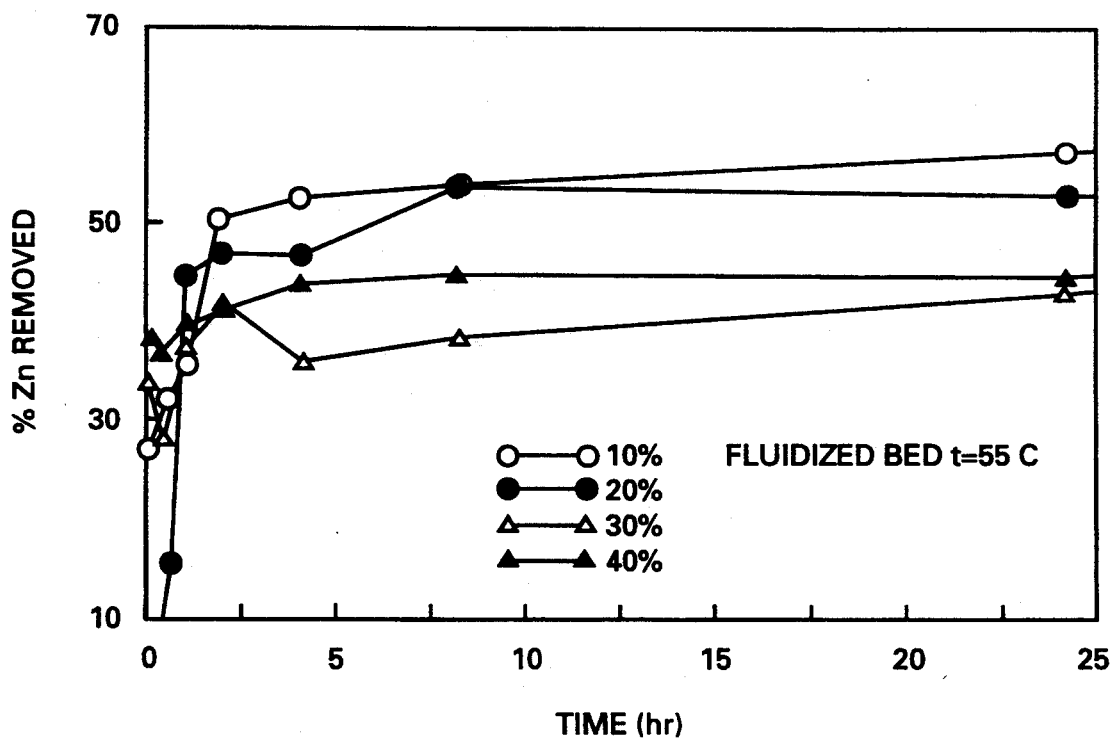
FIG. 22B graphically illustrates the removal of Zn from a residual brine in a fluidized bed at 55° C. over a period of 24 hrs.
Figure 23A:
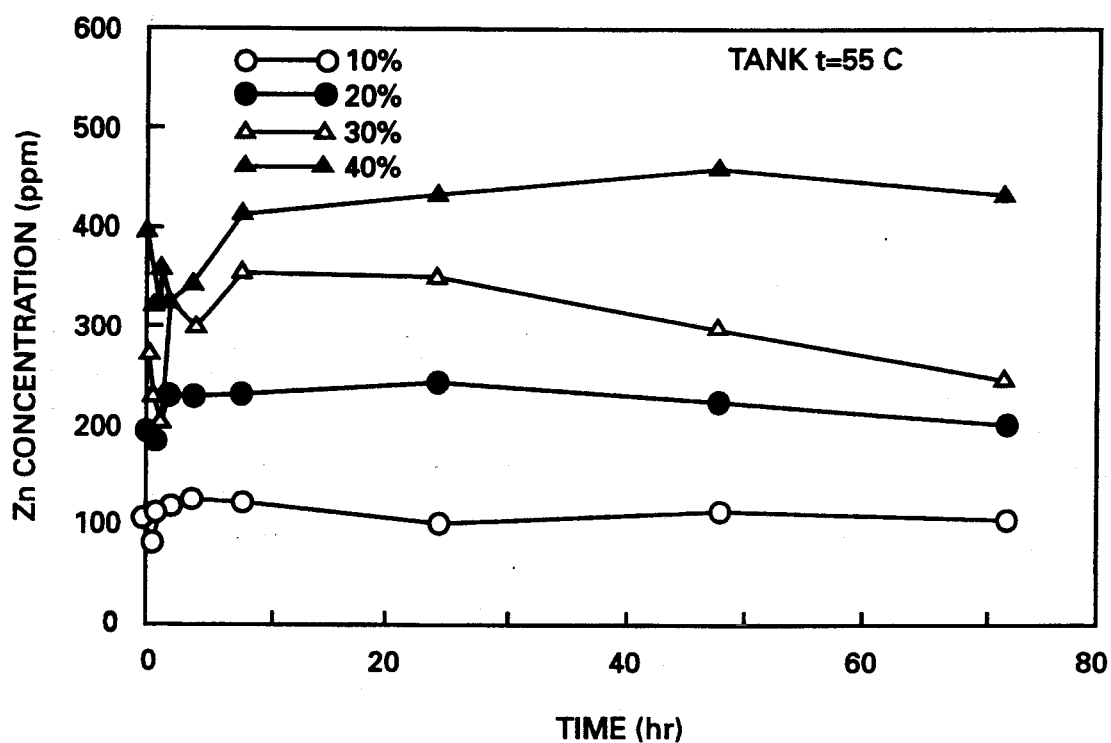
FIG. 23A graphically illustrates the change in zinc concentration after biotreatment of a residual brine in an agitated tank bioreactor at 55° C. over a 72 hour period, FIG. 23B graphically illustrates the change in zinc concentration after biotreatment of a residual brine in an agitated tank bioreactor at 55° C. over a 24 hour period.
Figure 23B:
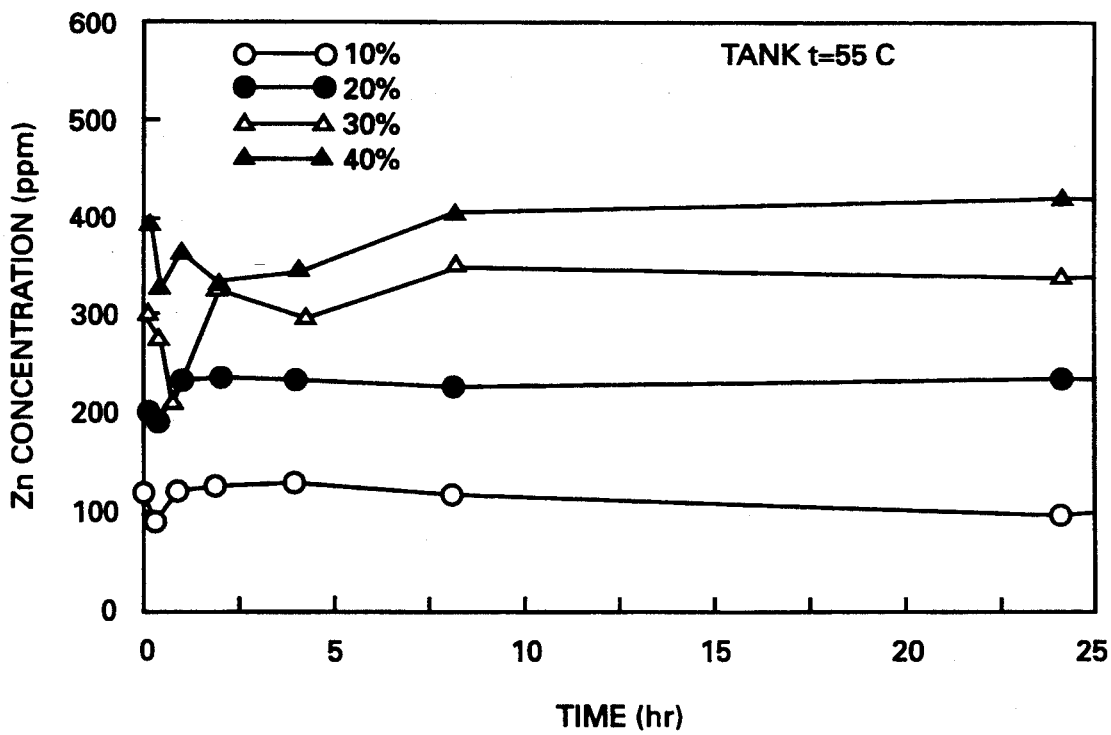
Figure 24A:
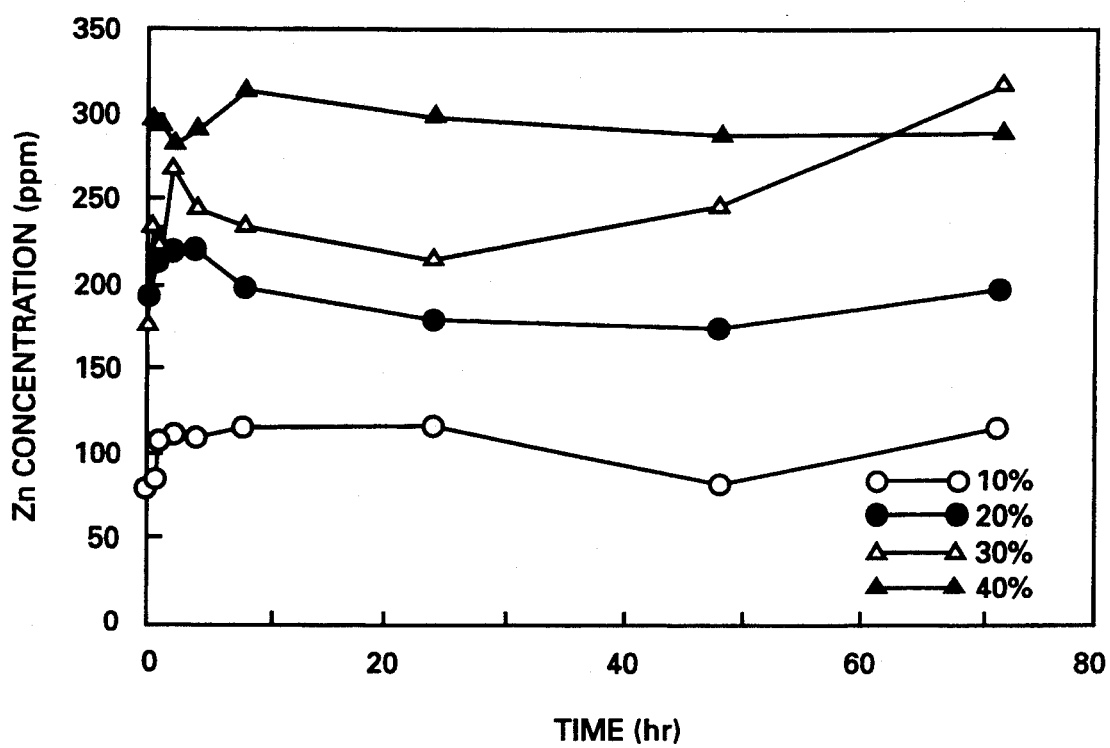
FIG. 24A graphically illustrates the change in zinc concentration after biotreatment of a residual brine in a fluidized bed at 55° C. over a 72 hour period.
Figure 24B:
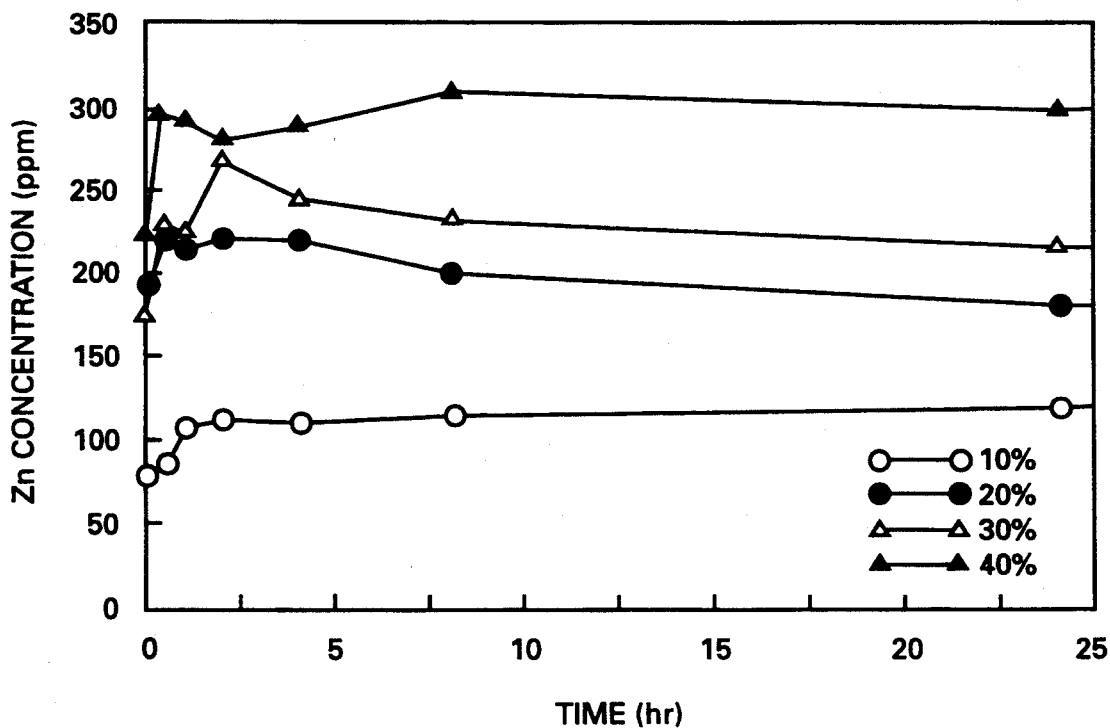
FIG. 24B graphically illustrates the change in zinc concentration after biotreatment of a residual brine in a fluidized bed at 55° C. over a 24 hour period.
Figure 25A:
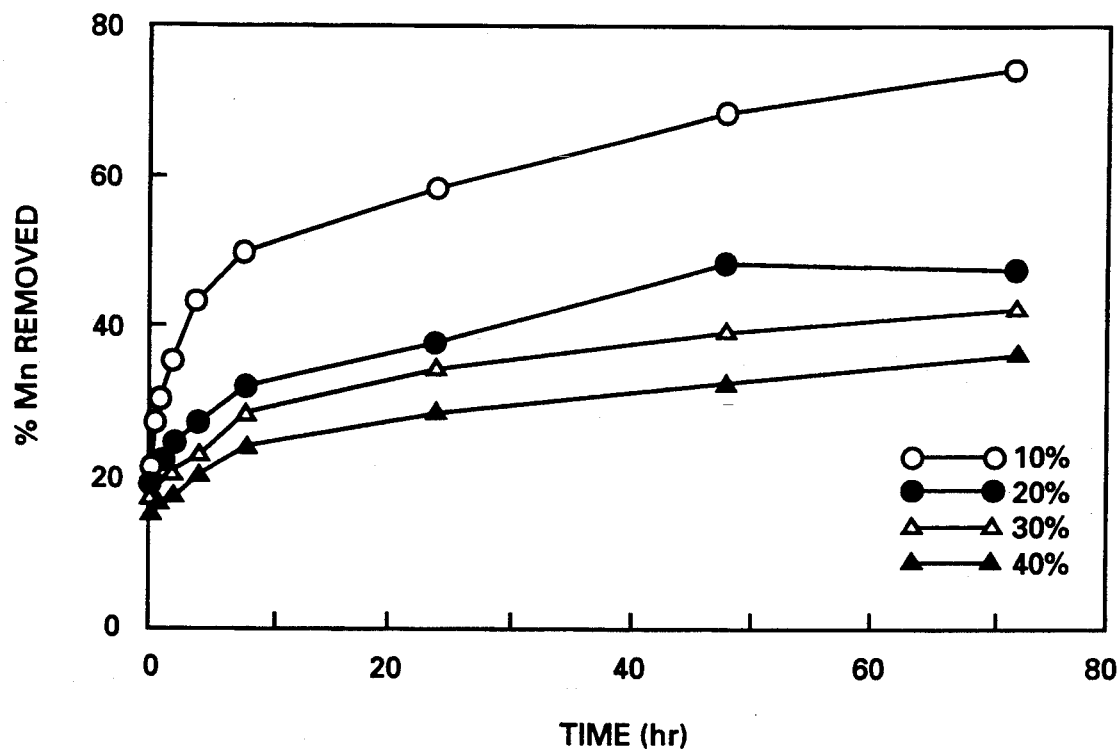
FIG. 25A graphically illustrates the removal of Mn from a residual brine in an agitated tank bioreactor at 55° C. over a period of 72 hrs.
Figure 25B:
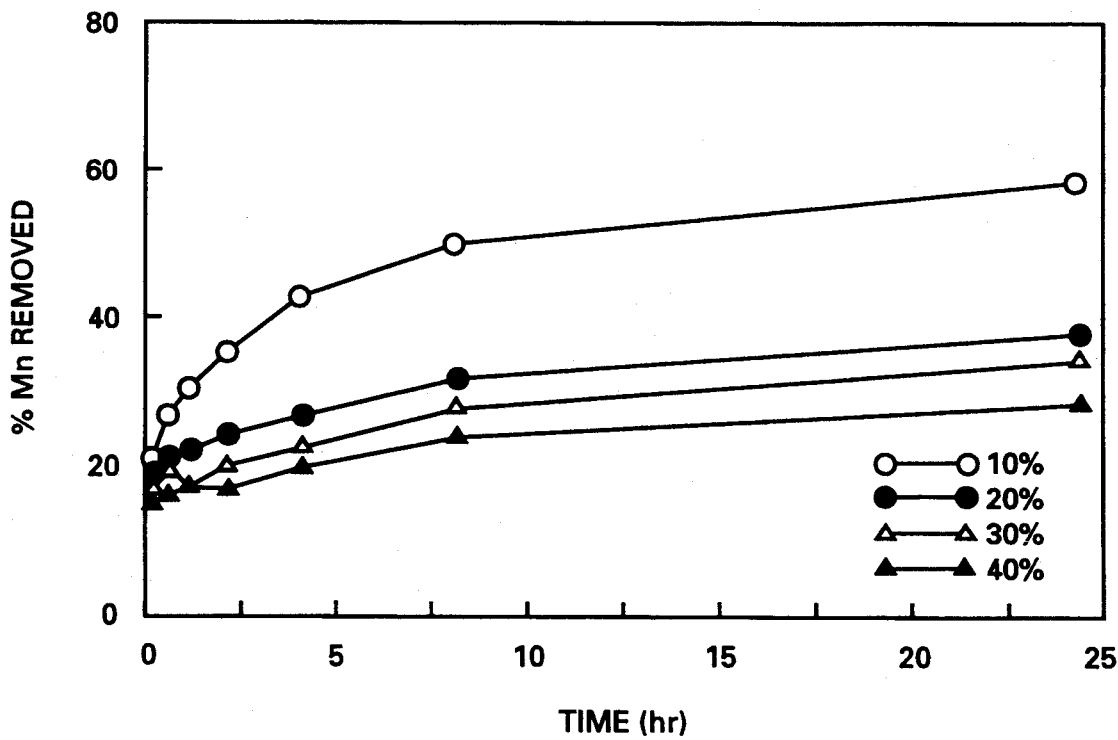
FIG. 25B graphically illustrates the removal of Mn from a residual brine in an agitated tank bioreactor at 55° C. over a period of 24 hrs.
Figure 26A:
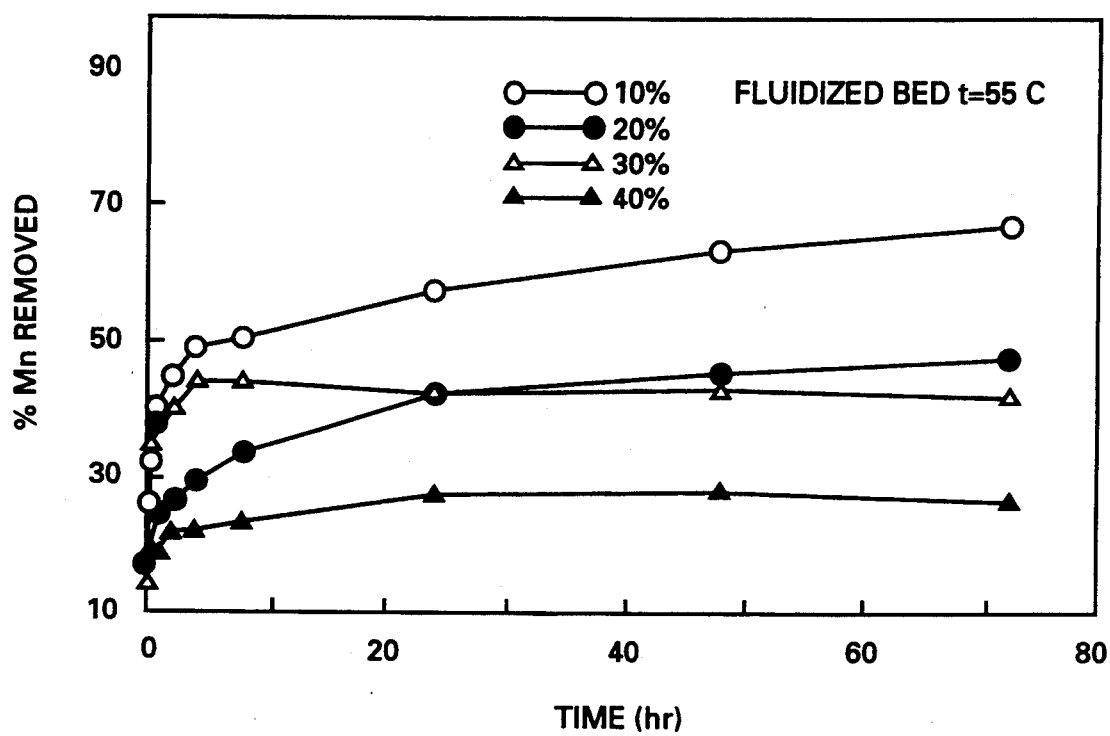
FIG. 26A graphically illustrates the removal of Mn from a residual brine in a fluidized bed at 55° C. over a period of 72 hrs.
Figure 26B:
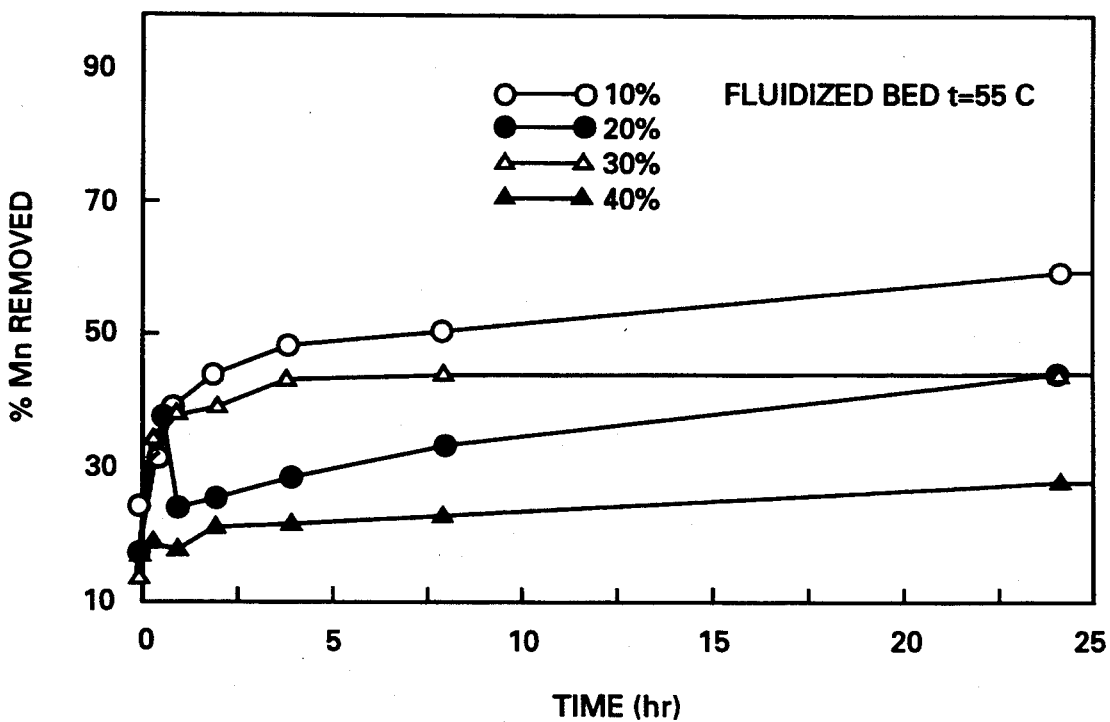
FIG. 26B graphically illustrates the removal of Mn from a residual brine in a fluidized bed at 55° C. over a period of 24 hrs.
Figure 27A:
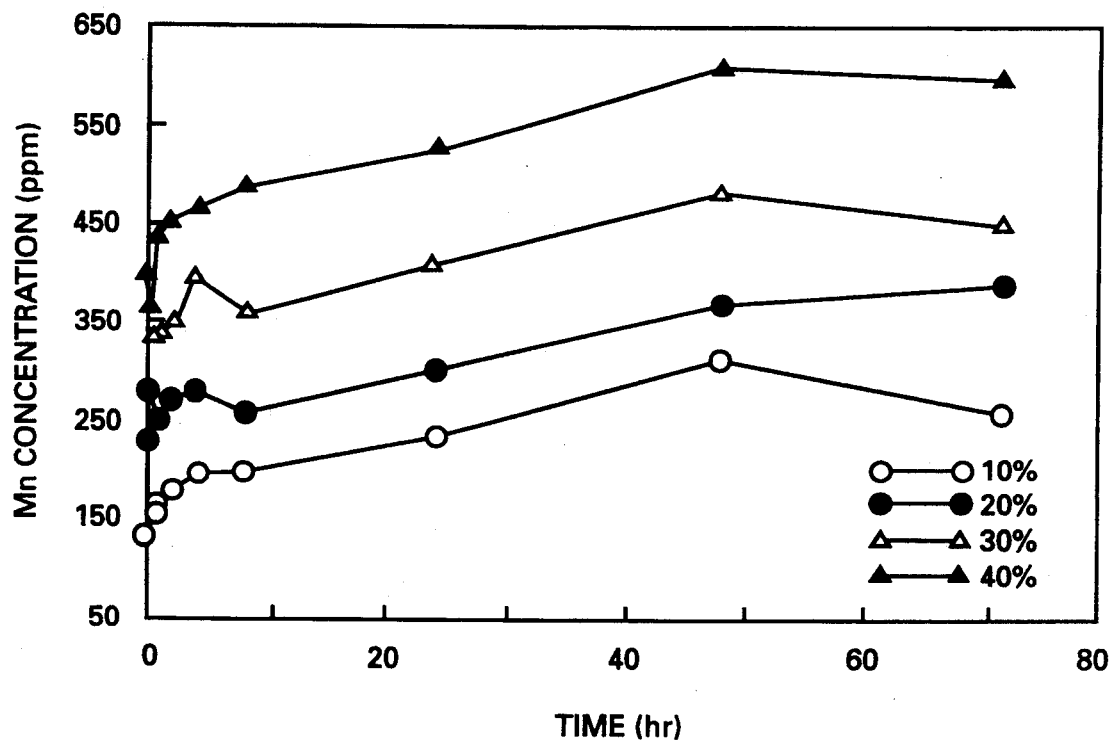
FIG. 27A graphically illustrates the change in manganese concentration after biotreatment of a residual brine in an agitated tank bioreactor at 55° C. over a 72 hour period.
Figure 27B:
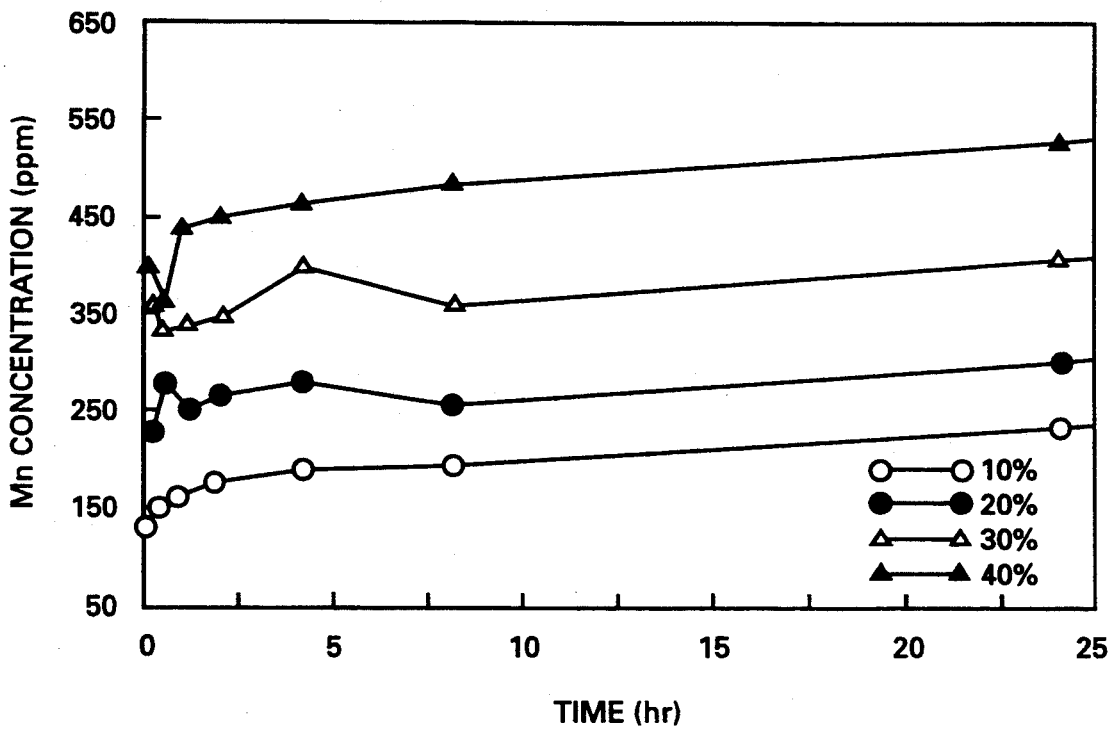
FIG. 27B graphically illustrates the change in manganese concentration after biotreatment of a residual brine in an agitated tank bioreactor at 55° C. over a 24 hour period.
Figure 28A:
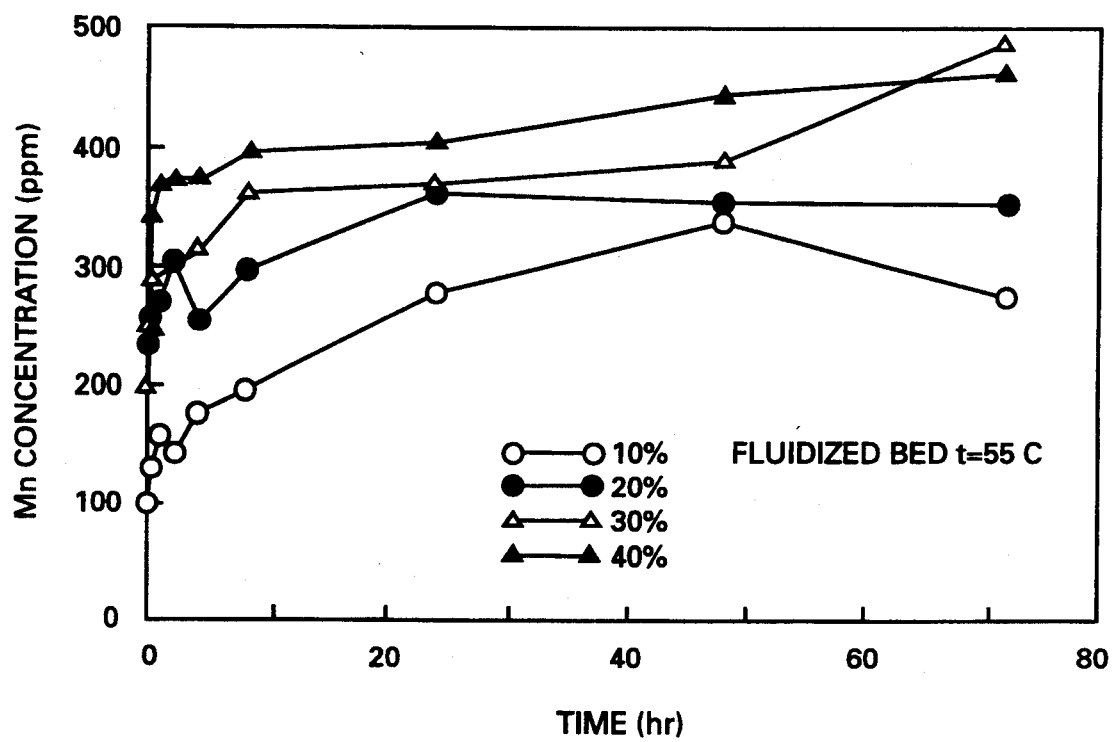
FIG. 28A graphically illustrates the change in manganese concentration after biotreatment of a residual brine in a fluidized bed at 55° C. over a 72 hour period.
Figure 28B:
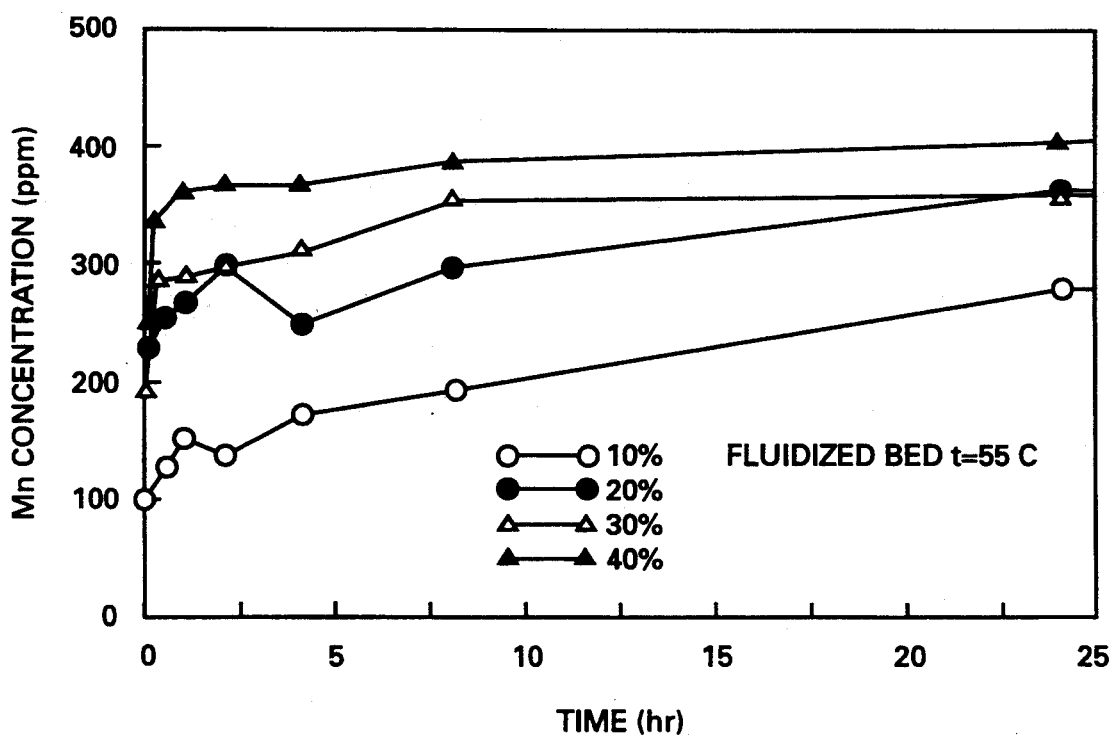
FIG. 28B graphically illustrates the change in manganese concentration after biotreatment of a residual brine in a fluidized bed at 55° C. over a 24 hour period.
Figure 29A:
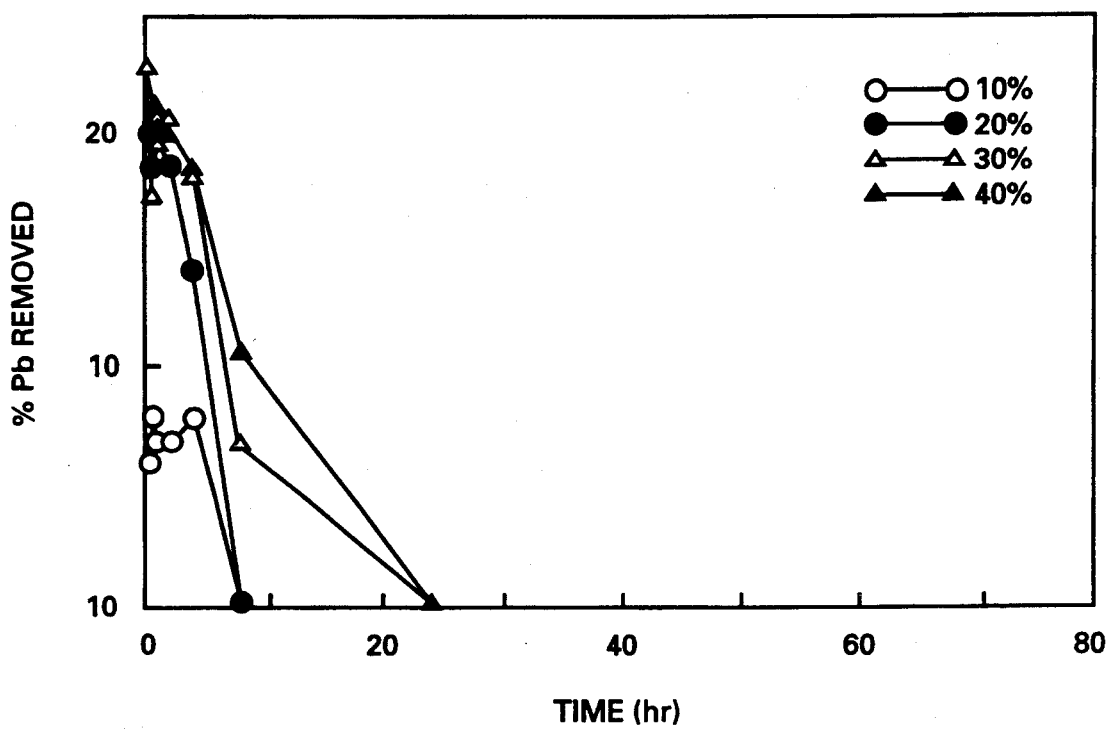
FIG. 29A graphically illustrates the removal of lead from a residual brine in an agitated tank bioreactor at 55° C. over a period of 72 hrs.
Figure 29B:
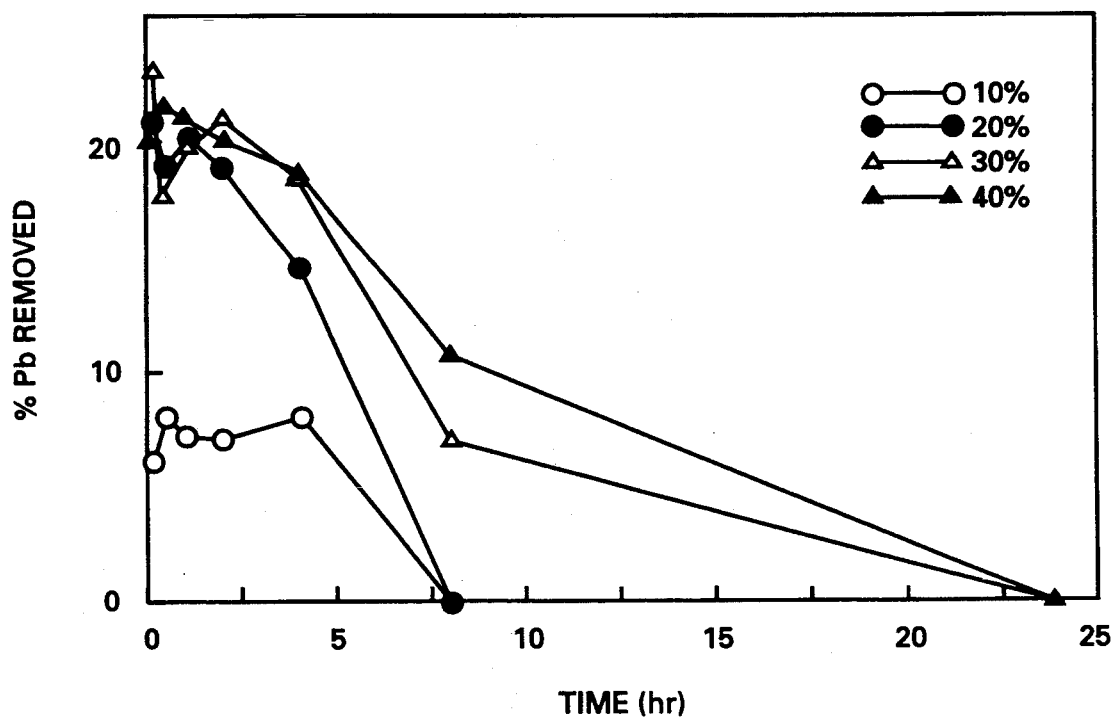
FIG. 29B graphically illustrates the removal of lead from a residual brine in an agitated tank bioreactor at 55° C. over a period of 24 hrs.
Figure 30A:
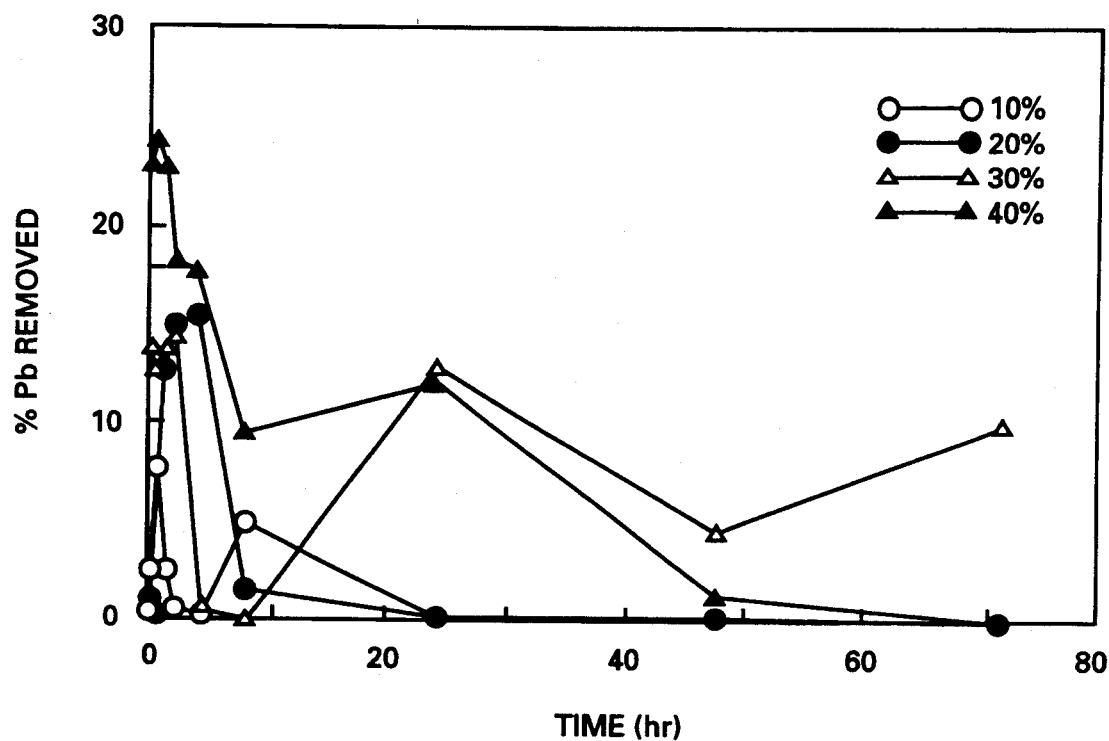
FIG. 30A graphically illustrates the removal of lead from a residual brine in a fluidized bed at 55° C. over a period of 72 hrs.
Figure 30B:
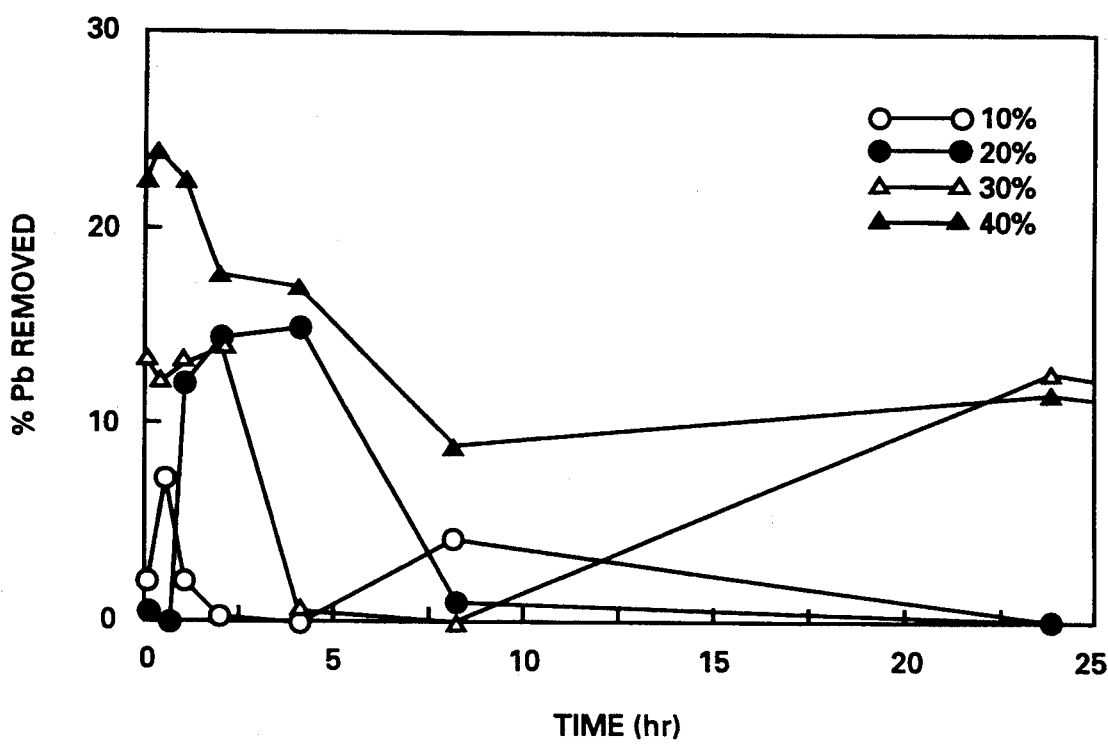
FIG. 30B graphically illustrates the removal of lead from a residual brine in a fluidized bed at 55° C. over a period of 24 hrs.
Figure 31A:
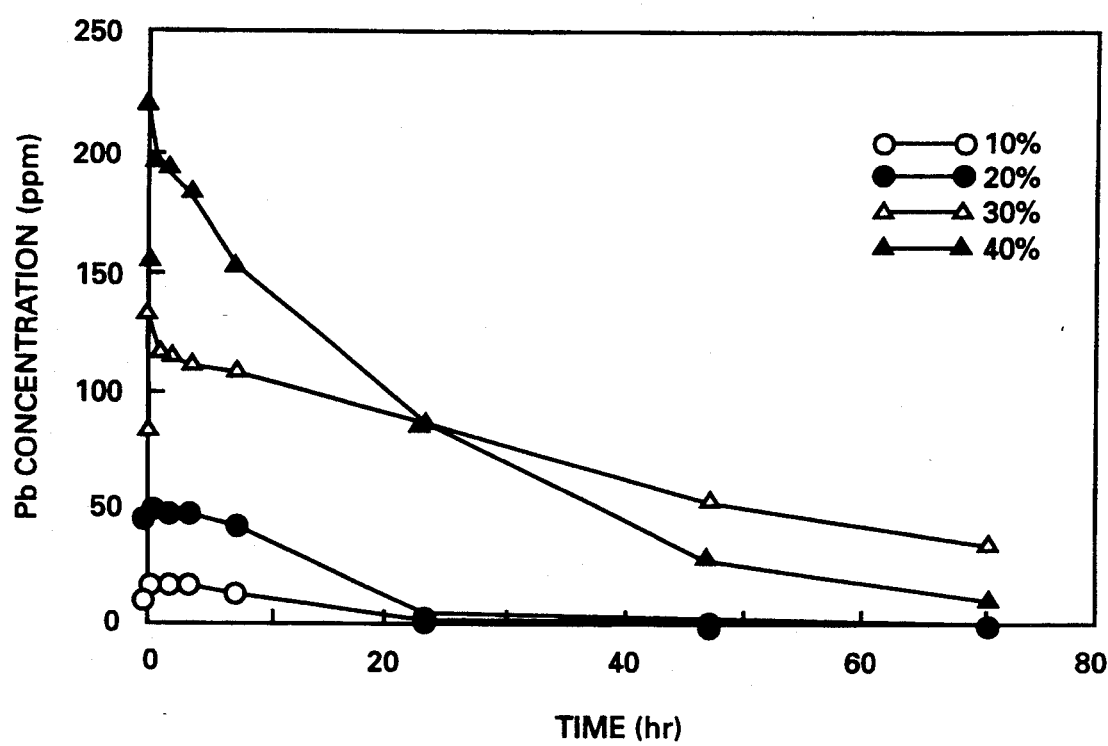
FIG. 31A graphically illustrates the change in lead concentration after biotreatment of a residual brine in an agitated tank bioreactor at 55° C. over a 72 hour period.
Figure 31B:
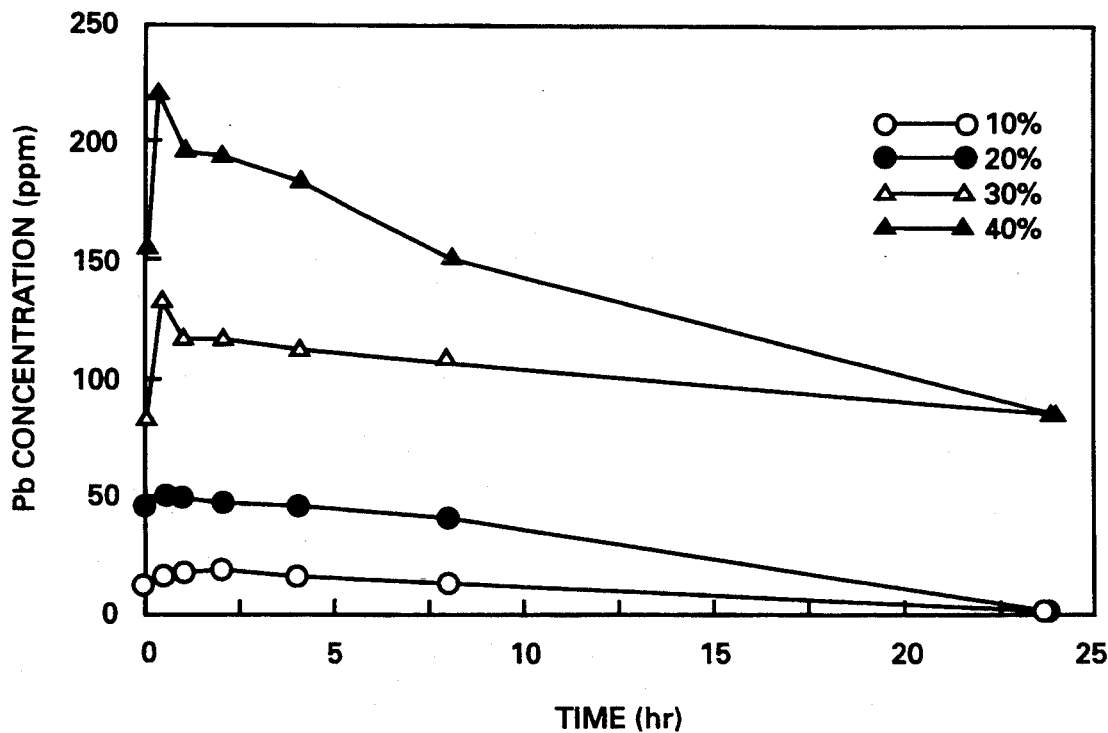
FIG. 31B graphically illustrates the change in lead concentration after biotreatment of a residual brine in an agitated tank bioreactor at 55° C. over a 24 hour period.
Figure 32A:
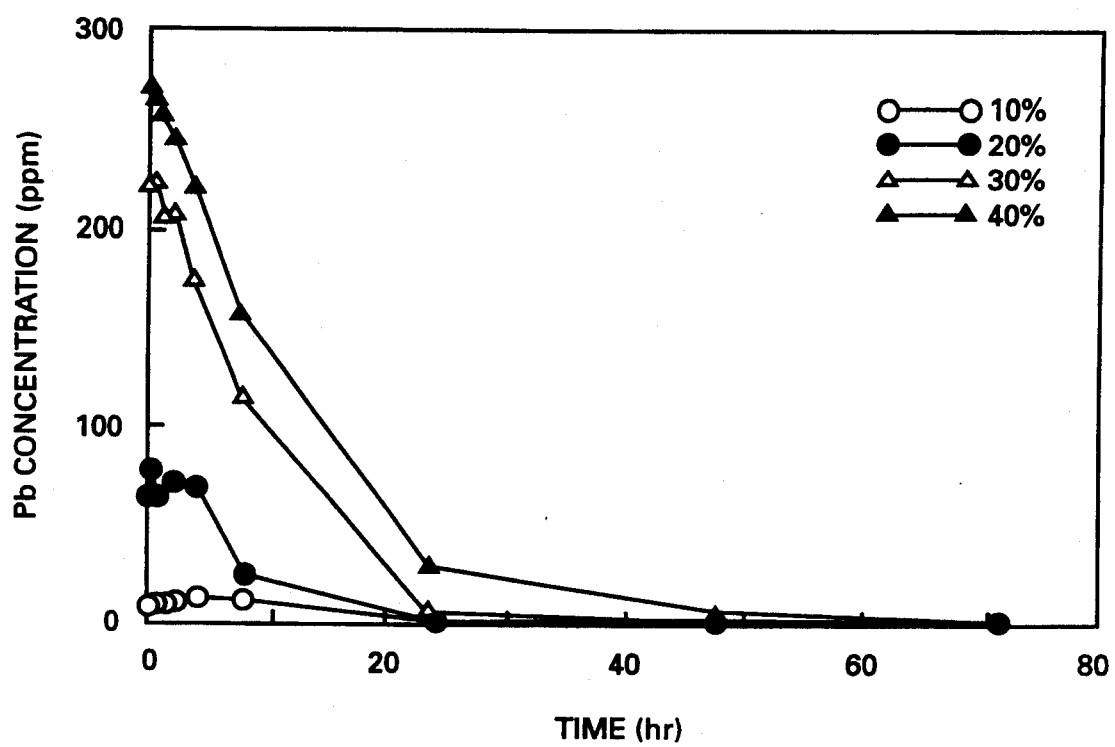
FIG. 32A graphically illustrates the change in lead concentration after biotreatment of a residual brine in a fluidized bed at 55° C. over a 72 hour period.
Figure 32B:
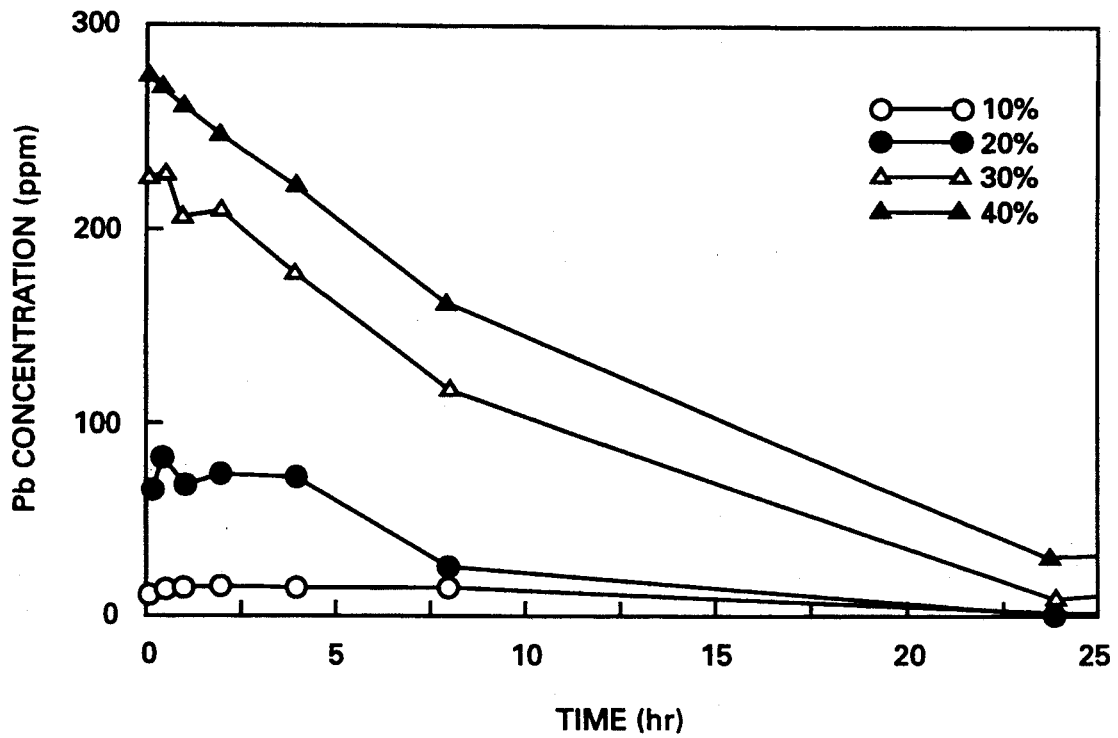
FIG. 32B graphically illustrates the change in lead concentration after biotreatment of a residual brine in a fluidized bed at 55° C. over a 24 hour period.

Four metals, copper, zinc, manganese, and lead were used as representative constituents of the geothermal residual brine sludge. In each case the data are presented for 0–80 hour and a 0–25 hour time interval (see FIGS. 5A and B, and 6A and B). Experiments were carried out with mixed cultures of temperature adapted *Thiobacillus thiooxidans* and *T. ferroxidans* at 55° C. and a pH range of 1-2. Analyses were performed on samples obtained from the solid and liquid phases in each bioreactor. Analysis of both the solid and liquid phase is a necessary step for the determination of material balance. Typical results for a single metal, e.g., copper, and different bioreactor loadings, e.g., 10%, 20%, 30%, and 40% are shown for solid and liquid phases in FIGS. 5–8. FIGS. 9 and 10 represent a summary of all the analyses at 40% loading with corresponding error bars as shown in the figures. There is an excellent agreement in the rate curves between the solid and liquid phases. High metal removal efficiency in time intervals of 25 hours are evident. Except for lead, after a 25 hour interval a steady state is reached. Because of solubility of lead sulfate formed, the initial and final concentrations of lead and sulfate ions are process (rate) limiting steps. However, the initial concentration of lead in the samples of geothermal residual sludge (2050 μg/g) used is such that even at a rate of 1% removal per hour over a period of twenty five hours, the concentration of lead remaining in the solid is below the total threshold limiting concentration (TTLC) as defined by regulatory agencies. The removal of other metals is also consistent with TTLC. Initially there is a rapid removal of metals, followed by a considerable drop in the rate of metals removal, indicating that several biochemical mechanisms are involved in the solubilization of metals from residual geothermal brines. Using the selected for mutant bacteria of the subject invention, a fast rate of metal removal is achieved at elevated temperatures and high sludge loadings. This brings the concentration of the metals to below the total threshold limitations. Accordingly, a single 25 hour cycle may be sufficient for the mixed high temperature Thiobacillus of the subject invention to function on a commercial scale.

In order to have a "quality control" handle for the system, a mass balance calculation has been carried out. In these calculations, the mass balance represented the total concentration of the metal in the solid and aqueous phases at the beginning of biotreatment and 72 hours later. Typical results are shown for zinc and copper in a fluidized bed (Table 3), and an agitated tank (Table 4). For all practical purposes, the net loss (−) and/or gain (+) is within the experimental error of analytical techniques used.

TABLE 3

Fluidized Bed Bioreactor
Mass balance for zinc and copper including a net gain/loss in grams per seventy-two hour cycle at 40% loading.

| Expt. No. | | Zn | Cu |
|---|---|---|---|
| 1 | 5 min. | 1.2470 | 0.4658 |
| | 72 h | 1.19350 | 0.4150 |
| | ± | 0.0535 (−) | 0.0508 (−) |
| 2 | 5 min. | 1.5380 | 0.6533 |
| | 72 h | 1.3842 | 0.5220 |
| | ± | 0.1538 (−) | 0.1313 (−) |
| 3 | 5 min. | 1.4070 | 0.5315 |
| | 72 h | 1.4278 | 0.4812 |
| | ± | 0.0208 (+) | 0.0503 (−) |

TABLE 4

Agitated and Tank Bioreactor
Mass balance for zinc and copper including a net gain/loss in grams per seventy-two hour cycle at 40% loading.

| Expt. No. | | Zn | Cu |
|---|---|---|---|
| 1 | 5 min. | 1.7280 | 0.5488 |
| | 72 h | 1.4909 | 0.46248 |
| | ± | 0.2371 (−) | 0.1243 (−) |
| 2 | 5 Min. | 1.9590 | 0.7208 |
| | 72 h | 1.523 | 0.5522 |
| | ± | 0.436 (−) | 0.1683 (−) |
| 3 | 5 min. | 1.6590 | 0.5338 |
| | 72 h | 1.4180 | 0.4777 |
| | + | 0.2410 (−) | 0.0561(−) |

In the removal of toxic metals from geothermal sludges, an aqueous effluent containing toxic metals is generated. The toxic metal content under field conditions does not cause any problems because the effluent can be reinjected. Efficiency of co-precipitation for several metals by chemical means is shown in Table 5. In this Table, percent removed means the total amount of metal precipitated from the aqueous phase produced after the biotreatment of geothermal residual brine sludge. For the metals tested the efficiency is remarkably high. By modifying the subject process, valuable metals found in the sludge may be recovered. A combined sludge detoxification-metal recovery process can offset the overall costs, since detoxified sludge may be used for landfill and other purposes, while metal concentrates would yield marketable metals.

TABLE 5

Removal of Metal from the Aqueous Phase

| | Treatment | | |
|---|---|---|---|
| | Scrap iron | Aluminum foil | Lime |
| Metal: Pb % removed | 83 | 88 | 94 |
| Metal: Mn % removed | 7.5 | 0.7 | 99 |
| Metal: Cr % removed | 94 | 95 | 96 |
| Metal: Cu % removed | 97 | 97 | 99 |
| Metal: Zn % removed | 4 | 10 | 99 |

For the following experiments, the microbial strains were grown in the media formulations specified in Table 6.

TABLE 6

Media Formulations for Thiobacillus Bacteria

| T. ferrooxidans | | T. thiooxidans | |
|---|---|---|---|
| Component | Amount | Component | Amount |
| $(NH_4)SO_4$ | 0.4 g | $(NH_4)_2SO_4$ | 0.2 g |
| $KH_2PO_4$ | 0.2 g | $KH_2PO_4$ | 3.0 g |
| $MgSO_4.7H_2O$ | 0.08 g | $MgSO_4.7H_2O$ | 0.5 g |
| $FeSO_4.7H_2O$ | 10.0 g | $CaCl_2$ | 0.25 g |
| $1N\ H_2SO_4$ | 1.0 ml | $FeSO_4$ | 0.005 g |
| Distilled Water | 500 ml | Tap Water | 1000 ml |

Different strains of Thiobacilli solubilize metals at different rates and efficiencies. This can be seen in FIGS. 11-16, where T.T. stands for *Thiobacillus thiooxidans* and T.F. stands for *Thiobacillus ferrooxidans*. As illustrated, the most efficient removers of metal sulfides comprise mixed cultures of selected strains of *Thiobacillus thiooxidans* and *Thiobacillus ferrooxidans*. Preferably, the microorganisms are grown separately to form a biomass which is added to the sludge containing bioreactor. Most preferably, the biomass is added to the sludge when the microorganisms are in the stage of maximum growth of approximately $1.7-2.6 \times 10^8$ cells/ml. If the cells are not added at the maximum growth stage, it is preferred that the reactor size be approximately 2 L for laboratory testing, as there will be a delay in achieving maximum growth as the size of the bioreactor increases. The pH may be adjusted by addition of an appropriate amount of an acidic compound such as $H_2SO_4$. The rate of metal sulfide solubilization increases with temperature. This is illustrated in FIGS. 17-32.

A series of batch kinetic experiments were conducted to determine the bacteria-catalyzed leaching rates of zinc and chromium from a residual geothermal sludge slurry (60 wt % solids). All chromium was assumed to be present in the hexavalent form. Hexavalent chromium is currently subject to the most stringent environmental regulations.

The waste sludge slurry BR-7 (60 wt % solids) was oven-dried overnight at 110° C. The cultures were grown under sterile conditions in defined media whose compositions are given in Table 6.

For sterile runs performed with *T. thiooxidans*, 1.0 g of powdered sulfur was placed in dry flasks and 100 ml of the appropriate culture medium was poured down the side of the flask without sinking the sulfur. For three consecutive days the flasks were sterilized in flowing steam for 30 minutes per day. The initial pH of the medium was approximately 4.2. Weighed amounts of sludge, autoclaved for sterility, were then added to the flasks. The mouths of the flasks were then plugged with sterile cotton.

For sterile runs performed with *T. ferrooxidans*, the medium was prepared from two solutions. The two solutions were separately autoclaved and then mixed at room temperature. One solution contained $FeSO_4$, $H_2SO_4$, and 100 ml of distilled water. The other solution contained the remaining nutrients listed in Table 6 and 400 ml of water. The pH was adjusted to 2.8 by the addition of 1N $H_2SO_4$. Weighed amounts of sludge were place in flasks and autoclaved. The mouth of each flask was flame sterilized and 100 ml of medium was added. The mouth of each flask was then plugged with sterile cotton.

The sludge and medium mixtures were inoculated under sterile condition with bacteria in 5 or 10 ml aliquots taken from stock cultures where the cell density had reached the exponential growth stage of approximately 1,000–10,000 cells/$mm^3$. Inoculation was performed within one hour after combining the sludge with the medium.

Sampling was performed immediately after inoculation by removing the cotton from the flask and inserting a sterile pipette to remove a 5.1 ml liquid sample. The cotton was then replaced with appropriate care to insure the sterility of the flask and medium. Approximately 0.1 ml of the sample was pipetted into a labelled 12.75 mm culture tube. The culture tube was then used for bacterial counts. The remaining 5 ml was pipetted into a clean labelled centrifuge tube. Each sample was then centrifuged to remove suspended sludge and cells from the liquid media. The supernatant from each sample was then filtered through a 0.22-micron filter into a labelled test tube to remove any remaining particulates. The pH of the samples was then determined by pipetting a small amount of leachate onto hydra-acid paper. Each sample was then analyzed in triplicate, both in solid and liquid phase by a Perkin-Elmer 560 Atomic Absorption spectrophotometer. Four metals, copper, zinc, manganese, and lead were used as representative constituents of the geothermal residual brine sludge and the analysis was conducted for these four metals. All growing cultures were sampled every 24–48 hr thereafter for bacterial growth and Pb, Zn, Cu and Mn concentration measurements.

The standard conditions used to grow bacteria were: (1) 26° C., (2) shaker agitation (3) sterility, (4) 100 ml of media as recommended by the ATCC, and (5) no air bubbling.

The results of all the analyses are given in FIGS. 17–32. In each case the data are presented for 0–80 h and a 0–25 h time interval. All the experiments have been carried out with mixed cultures of temperature adapted *Thiobacillus thiooxidans* and *T. ferroxidans* at 55° C. and a pH range of 1–2. Analyses have been carried out on samples obtained from the solid and liquid phases in each bioreactor, viz., tank or fluidized bed used. Analysis of both the solid and liquid phase is a necessary step for the determination of material balance. There is an excellent agreement in the rate curves between the solid and liquid phases. High metal removal efficiency in time intervals of 25 hours are evident. Except for lead, after a 60–80% metal removal a steady state is reached. In the case of lead, because of solubility of lead sulfate formed, the initial and final concentrations of lead and sulfate ions are process limiting steps. However, the initial concentration of lead in the samples of geothermal residual sludge (2050 μg/g) used is such that even at a rate of 1% removal per hour over a period of twenty five hours, the concentration of lead remaining in the solid is below the total threshold limiting concentration (TTLC) as defined by regulatory agencies.

Upon reading the subject specification, various modifications and alternative embodiments will become obvious to those skilled in the art. These embodiments are to be considered within the scope and spirit of the subject invention. Accordingly, the subject invention is only to be limited by the claims which follow and their equivalents.

We claim:

1. A process for the dissolution and removal of metal salts in geothermal brine or sludge which comprises:
   (a) preparing a mixture of microorganisms which mixture contains at least one Thiobacillus which solubilizes metal salts at elevated temperatures of at least about 50° C.;
   (b) contacting the geothermal brine or sludge which comprises metal salts with the microorganism mixture in an aqueous environment at a temperature of at least about 50° C.;
   (c) incubating the geothermal brine or sludge with the microorganism mixture under conditions and for a period of time sufficient to solubilize the metal salts to form solubilized metal; and
   (d) removing said solubilized metal so that the concentration of metal salts in the brine or sludge is reduced.

2. A process of claim 1, wherein the Thiobacillus is a *Thiobacillus ferrooxidans* selected from the group consisting of ATCC #53982, ATCC #53983, ATCC #53984, ATCC #53985, ATCC #53986 and ATCC #53987.

3. A process of claim 1, wherein the Thiobacillus is a *Thiobacillus thiooxidans* selected from the group consisting of ATCC #55019, ATCC #55020, ATCC #53990 and ATCC #55009.

4. A process of claim 2, wherein the *Thiobacillus ferrooxidans* is ATCC#53987.

5. A process of claim 3, wherein the *Thiobacillus thiooxidans* is ATCC #55020.

6. A process of claim 1, wherein the incubation period is from about 14 hours to about 25 hours.

7. A process of claim 1, wherein the microorganism mixture is grown separately to maximum growth and then added to the geothermal brine or sludge.

8. A process of claim 1, wherein the aqueous environment is acidic.

9. A process of claim 8, wherein the aqueous environment has a pH of from about 1.0 to about 2.0.

10. The process of claim 1, wherein the temperature of the aqueous environment is from about 50° C. to about 80° C.

11. The process of claim 10 wherein the temperature is from about 50° C. to about 60° C.

12. A biologically pure culture of *Thiobacillus ferrooxidans* ATCC 53987.

13. A biologically pure culture of *Thiobacillus thiooxidans* ATCC 55020.

* * * * *